US009662042B2

(12) United States Patent
Akimoto et al.

(10) Patent No.: US 9,662,042 B2
(45) Date of Patent: May 30, 2017

(54) ENDOSCOPE SYSTEM FOR PRESENTING THREE-DIMENSIONAL MODEL IMAGE WITH INSERTION FORM IMAGE AND IMAGE PICKUP IMAGE

(71) Applicant: OLYMPUS CORPORATION, Tokyo (JP)

(72) Inventors: Syunya Akimoto, Kawasaki (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/948,804

(22) Filed: Nov. 23, 2015

(65) Prior Publication Data
US 2016/0073927 A1    Mar. 17, 2016

Related U.S. Application Data

(63) Continuation of application No. PCT/JP2014/073907, filed on Sep. 10, 2014.

(30) Foreign Application Priority Data

Oct. 2, 2013    (JP) .................................. 2013-207456

(51) Int. Cl.
*A61B 1/04*    (2006.01)
*A61B 5/06*    (2006.01)
(Continued)

(52) U.S. Cl.
CPC ............ *A61B 5/066* (2013.01); *A61B 1/0005* (2013.01); *A61B 1/00009* (2013.01); *A61B 1/05* (2013.01);
(Continued)

(58) Field of Classification Search
CPC ..... A61B 1/00009; A61B 1/0005; A61B 1/05; A61B 1/06; A61B 1/307; A61B 1/00181;
(Continued)

(56) References Cited

U.S. PATENT DOCUMENTS

| 2004/0249247 | A1* | 12/2004 | Iddan | ................... A61B 1/0005 600/170 |
| 2005/0113643 | A1* | 5/2005 | Hale | ................... A61B 1/00009 600/118 |

(Continued)

FOREIGN PATENT DOCUMENTS

| EP | 2700351 A1 | 2/2014 |
| JP | 2003-225195 A | 8/2003 |

(Continued)

OTHER PUBLICATIONS

International Search Report dated Dec. 9, 2014 issued in PCT/JP2014/073907.

(Continued)

*Primary Examiner* — John P Leubecker
(74) *Attorney, Agent, or Firm* — Scully, Scott, Murphy & Presser, P.C.

(57) ABSTRACT

The endoscope system includes: an endoscope including an insertion portion to be inserted into a subject, and an image pickup portion that picks up an image of inside of the subject; an image pickup information acquisition portion that acquires positional information of the image pickup portion; an insertion form information acquisition portion that acquires insertion form information of the insertion portion inside the subject; and a control portion that, on a stereoscopic model image that simulates a predetermined organ inside the subject, superimposes an insertion form image that is based on insertion form information that is acquired by the insertion form information acquisition portion, and based on positional information of the image (Continued)

pickup portion that is acquired by the image pickup information acquisition portion, also pastes an image pickup image that is picked up by the image pickup portion, and presents the resulting stereoscopic model image.

12 Claims, 18 Drawing Sheets

(51) Int. Cl.
    *A61B 1/00*     (2006.01)
    *A61B 1/05*     (2006.01)
    *A61B 1/06*     (2006.01)
    *A61B 1/307*     (2006.01)
    *G06T 19/00*     (2011.01)
    *A61B 34/20*     (2016.01)

(52) U.S. Cl.
    CPC .............. *A61B 1/06* (2013.01); *A61B 1/307* (2013.01); *G06T 19/00* (2013.01); *A61B 1/0638* (2013.01); *A61B 2034/2051* (2016.02); *G06T 2207/10068* (2013.01); *G06T 2210/41* (2013.01)

(58) Field of Classification Search
    CPC ... A61B 1/00183; A61B 1/0638; A61B 5/066; A61B 5/7425; G06T 19/006; G06T 11/60; G06T 7/0046; G06T 2207/10068; G06T 2207/20212
    See application file for complete search history.

(56) References Cited

U.S. PATENT DOCUMENTS

| | | | | |
|---|---|---|---|---|
| 2007/0149846 | A1* | 6/2007 | Chen | A61B 1/00009 600/117 |
| 2009/0259102 | A1* | 10/2009 | Koninckx | A61B 1/00181 600/111 |
| 2010/0249506 | A1* | 9/2010 | Prisco | A61B 1/00009 600/117 |
| 2011/0242301 | A1* | 10/2011 | Morita | A61B 1/00009 348/65 |
| 2012/0287238 | A1* | 11/2012 | Onishi | A61B 1/0005 348/45 |
| 2012/0289825 | A1* | 11/2012 | Rai | A61B 6/463 600/425 |
| 2013/0109915 | A1 | 5/2013 | Krupnik et al. | |
| 2014/0088357 | A1 | 3/2014 | Ikuma et al. | |
| 2014/0296644 | A1* | 10/2014 | Zilberstein | A61B 1/06 600/178 |
| 2015/0025316 | A1* | 1/2015 | Hasegawa | A61B 1/04 600/109 |
| 2015/0305600 | A1* | 10/2015 | Minamizato | A61B 1/005 600/111 |
| 2016/0000307 | A1* | 1/2016 | Akimoto | A61B 1/04 600/109 |

FOREIGN PATENT DOCUMENTS

| | | |
|---|---|---|
| JP | 2007-159641 A | 6/2007 |
| JP | 2010-240000 A | 10/2010 |
| JP | 2010-256988 A | 11/2010 |
| JP | 2011-036600 A | 2/2011 |
| JP | 2013-524988 A | 6/2013 |
| WO | WO 2011/135573 A1 | 11/2011 |
| WO | WO 2013/132880 A1 | 9/2013 |
| WO | WO 2014/136579 A1 | 9/2014 |

OTHER PUBLICATIONS

Hakamata, Shinichi et al., "Reconstruction of 3D organ image using endoscope with Magneto-position-sensor", IEICE Technical Report, MI, Jun. 30, 2006, vol. 106, No. 145, pp. 13-18, together with English Abstract.

* cited by examiner

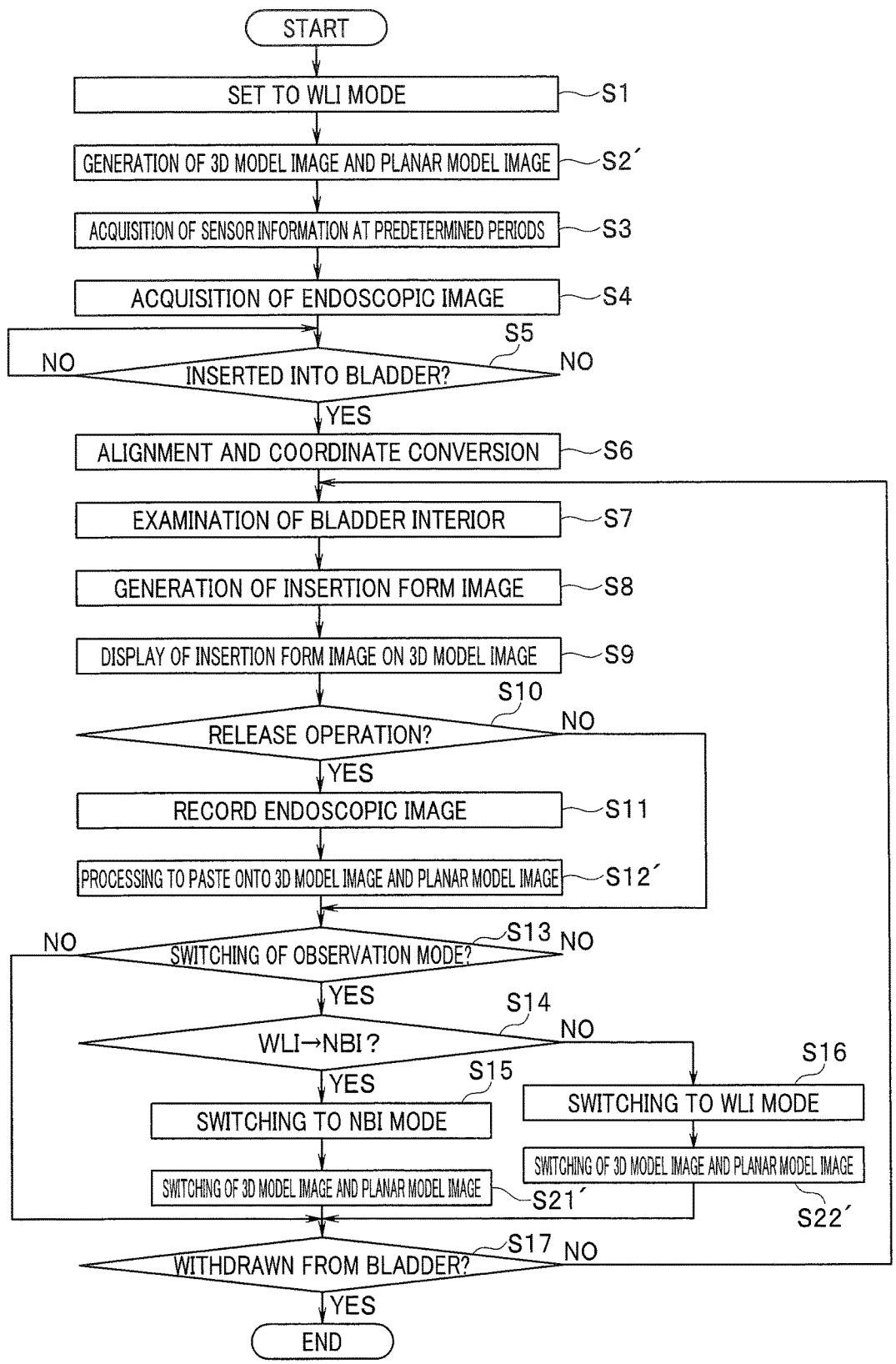

(A)

(B)

ENDOSCOPE SYSTEM FOR PRESENTING THREE-DIMENSIONAL MODEL IMAGE WITH INSERTION FORM IMAGE AND IMAGE PICKUP IMAGE

CROSS REFERENCE TO RELATED APPLICATION

This application is a continuation application of PCT/JP2014/073907 filed on Sep. 10, 2014 and claims benefit of Japanese Application No. 2013-207456 filed in Japan on Oct. 2, 2013, the entire contents of which are incorporated herein by this reference.

BACKGROUND OF THE INVENTION

1. Field of the Invention

The present invention relates to an endoscope system that observes an inside of a predetermined organ of a subject.

2. Description of the Related Art

Endoscopes equipped with image pickup means have been widely used in a medical field and the like in recent years. Further, since the shape of an organ or the like inside a subject into which an insertion portion of an endoscope is inserted cannot be known using an endoscope, in some cases an X-ray apparatus is used in combination with an endoscope so that the insertion state can be ascertained and a lesion position can be identified.

In this connection, for example, in Japanese Patent Application Laid-Open Publication No. 2003-225195 as a first conventional example, a monitor apparatus is disclosed that, without combining the use of an X-ray apparatus, displays a bending form of an insertion portion of an endoscope on a monitor screen and also displays a shape of an organ into which the insertion portion is inserted, and furthermore corrects the shape of the organ.

Further, Japanese Patent Application Laid-Open Publication No. 2010-240000 as a second conventional example discloses a system in which an image of the inside of a body cavity is picked up by an image pickup portion of a capsule endoscope, and based on image data acquired by the capsule endoscope, an image processing apparatus generates a diagnostic image that is a three-dimensional model of the inside of the body cavity. More specifically, the aforementioned second conventional example discloses generating a 3D image for diagnosis by pasting an image that is picked up by a capsule endoscope on an existing three-dimensional model (image) for respective sites such as the "stomach" and "small intestine".

SUMMARY OF THE INVENTION

An endoscope system according to one aspect of the present invention includes: an endoscope including an insertion portion to be inserted into a subject, and an image pickup portion that picks up an image of inside of the subject; an image pickup information acquisition portion that acquires positional information of the image pickup portion; an insertion form information acquisition portion that acquires insertion form information of the insertion portion inside the subject; and a control portion that, on a stereoscopic model image that simulates a predetermined organ inside the subject, superimposes an insertion form image that is based on the insertion form information acquired by the insertion form information acquisition portion, and based on positional information of the image pickup portion that is acquired by the image pickup information acquisition portion, also pastes an image pickup image that is picked up by the image pickup portion, and presents the stereoscopic model image.

BRIEF DESCRIPTION OF THE DRAWINGS

FIG. 16B is a flowchart illustrating a processing example according to a first modification of the fourth embodiment;

DETAILED DESCRIPTION OF THE PREFERRED EMBODIMENTS

Embodiments of the present invention are described hereunder with reference to the accompanying drawings.

First Embodiment

Figure 1:
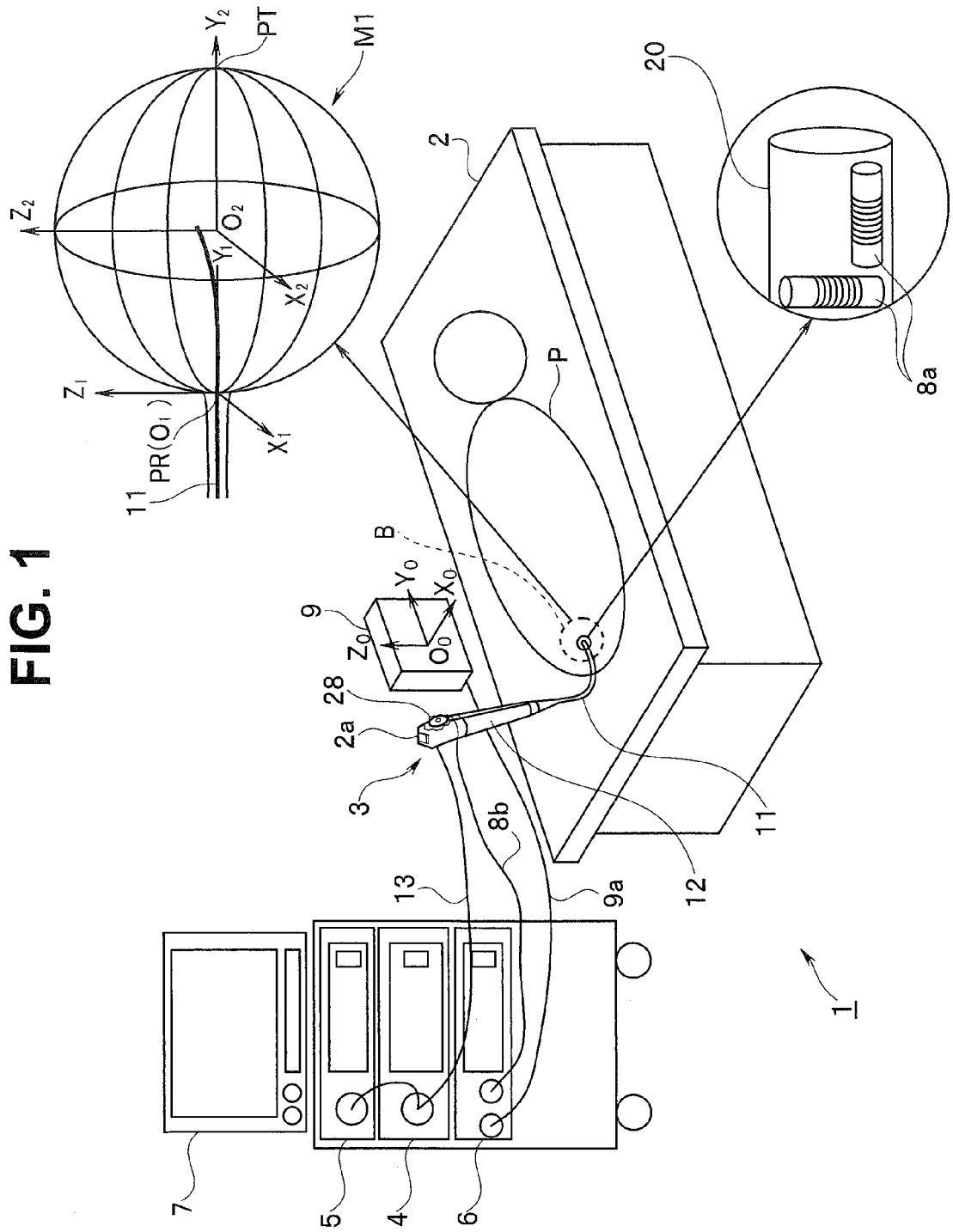
FIG. 1 is a perspective view illustrating the overall configuration of an endoscope system of a first embodiment of the present invention.

As shown in FIG. 1, an endoscope system 1 of the first embodiment of the present invention includes: an endoscope 3 for inserting into a patient P as a subject lying on a bed 2 to perform observation or examination; a light source apparatus 4 that supplies an illuminating light to the endoscope 3; a processor 5 as a signal processing apparatus that performs signal processing with respect to image pickup means (or an image pickup portion) of the endoscope 3; an image processing apparatus 6 that performs image processing and recording or the like with respect to an image (or image signal) generated by the processor 5; a monitor 7 that displays an endoscopic image (or image pickup image) generated by the processor 5 and an image that underwent image processing by the image processing apparatus 6; and a magnetic field generating apparatus 9 that detects a position of a magnetic sensor 8 that is provided in the vicinity of the image pickup means.

The endoscope 3 includes an insertion portion 11 which is flexible, an operation portion 12 that is provided at a rear end (proximal end) of the insertion portion 11 and is grasped by a surgeon to perform operations such as bending, and a universal cable 13 that is extended from the operation portion 12.

Figure 2:
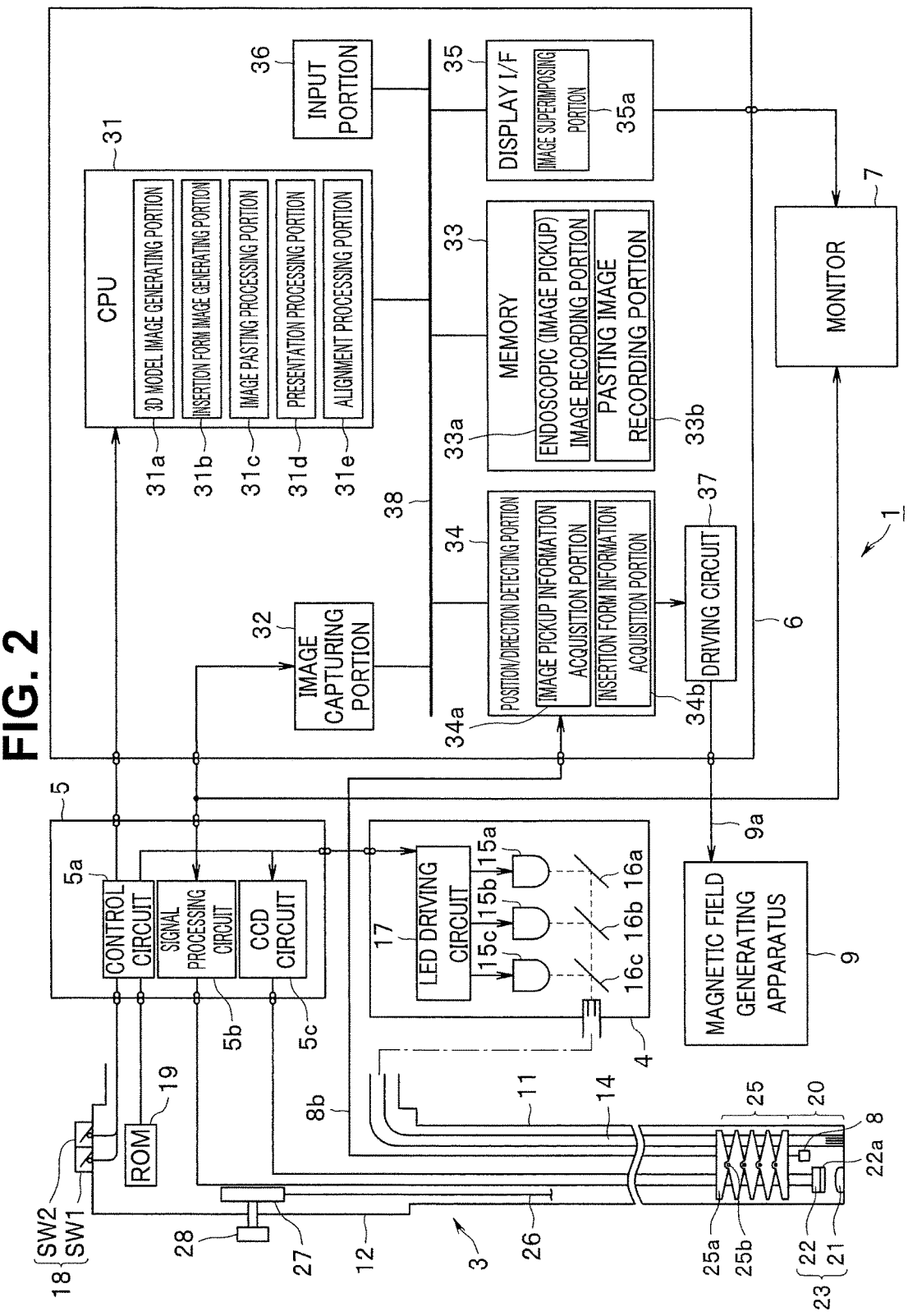
FIG. 2 is a view illustrating the internal configuration of the endoscope system of the first embodiment of the present invention.

Further, as shown in FIG. 2, a light guide 14 that transmits an illuminating light is inserted through the inside of the insertion portion 11. The light guide 14 passes from the operation portion 12 to universal cable 13 and a light guide connector at a hand-side end portion of the light guide 14 is detachably connected to the light source apparatus 4. Note that a signal wire 24 that is connected to an image pickup portion 23 that is mounted inside a distal end portion 20 that is described later passes through the universal cable 13 and a signal connector that is a hand-side end portion of a signal wire 24 is detachably connected to the processor 5.

The light source apparatus 4 in the present embodiment has a function for switching between and outputting (generating) normal light and narrow band light as special light. As shown in FIG. 2, light emitting diodes (abbreviated as "LEDs") 15a, 15b and 15c, mirrors 16a, 16b and 16c, and an LED driving circuit 17 are provided inside the light source apparatus 4. The LED 15a generates white light which, after being reflected by the mirror 16a, passes through the dichroic mirrors 16b and 16c and enters the hand-side end portion of the light guide 14.

The LEDs 15b and 15c generate blue light (Bn) and green light (Gn) of a narrow band whose center wavelengths are set in the vicinity of 415 nm and the vicinity of 540 nm, respectively. The narrow band light Bn generated by the LED 15b is selectively reflected by the dichroic mirror 16b, and thereafter passes through the dichroic mirror 16c and enters the end portion of the light guide 14.

Figure 3:
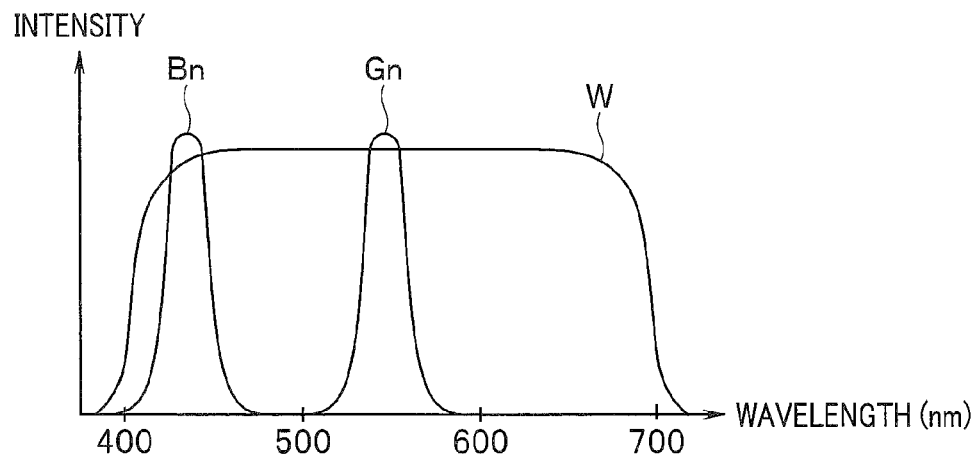
FIG. 3 is a characteristics diagram illustrating a wavelength distribution of illuminating light that the light source apparatus generates.

The narrow band light Gn generated by the LED 15c is selectively reflected by the dichroic mirror 16c, and thereafter enters the hand-side end portion of the light guide 14. FIG. 3 illustrates an example of characteristics of the wavelength distribution of white light W that the LED 15a generates and the wavelength distribution of the narrow band lights Bn and Gn generated by the LEDs 15b and 15c, respectively.

Although in the present embodiment a configuration is adopted that generates the white light W as normal light and generates the two narrow band lights Bn and Gn as special light, the present invention is not limited thereto. For example, a configuration may be adopted that generates the narrow band light Bn or Gn as special light, or a configuration may be adopted that generates excitation light and observes fluorescence.

A scope switch 18 that includes a mode switching switch SW1 that performs an operation to switch from one observation mode among a normal light observation mode (or white light observation mode; also referred to as "WLI mode") and a narrow band light observation mode (also referred to as "NBI mode") to the other observation mode, and a release switch SW2 that performs a release operation are provided in the operation portion 12 of the endoscope 3.

When the mode switching switch SW1 is operated by a surgeon who grasps the operation portion 12 of the endoscope 3, a switching signal is sent to a control circuit 5a inside the processor 5 and to the light source apparatus 4 by passing through the control circuit 5a. In the light source apparatus 4, the LED driving circuit 17 switches light emission between the LED 16a and the LEDs 16b and 16c in accordance with the switching signal. Furthermore, the processor 5 performs signal processing that corresponds to the switching signal.

A release instruction signal in a case where the release switch SW2 is operated passes through the (control circuit 5a inside the) processor 5 and is inputted to a central processing unit (abbreviated as "CPU") 31 that constitutes control means (or a control portion) inside the image processing apparatus 6, and the CPU 31 performs a control operation to record an endoscopic image.

Note that, the endoscope 3 that is detachably connected to the processor 5 includes a ROM 19 inside the signal connector or the operation portion 12. The ROM 19 is provided as a read-only memory that forms image pickup system information storing means (or an image pickup system information storing portion) that stores information such as a focal distance and a view angle (field of view range) as information of the image pickup system of the image pickup portion 23 that constitutes image pickup means that is mounted in the endoscope 3. When the signal connector of the endoscope 3 is connected to the processor 5, the control circuit 5a of the processor 5 reads out data of the ROM 19 and sends the data that is read to the CPU 31. Note that a recording medium other than the ROM 19 may also be used.

The CPU 31 acquires information regarding the image pickup system of the image pickup portion 23 from the data that is transferred from the processor 5, and refers to the information as necessary. Note that a configuration may also be adopted in which the ROM 19 does not store information regarding the image pickup system, and instead stores an ID as identification information that is unique to the endoscope 3, and information regarding the image pickup system of the image pickup portion 23 that is mounted in the endoscope 3 that corresponds to the ID can be acquired based on the ID that is read out by the processor 5.

The illuminating light that entered the hand-side end portion of the light guide 14 is transferred to a distal end face thereof by the light guide 14. The distal end face of the light guide 14 is disposed in an illuminating window provided in the distal end portion 20 of the insertion portion 11, and emits the illuminating light through the illuminating window to the subject side that is on the outside of the illuminating window. The light source apparatus 4 and light guide 14 form illumination means (or an illumination portion) for switching between normal light and special light and irradiating the relevant light to the subject side to illuminate the subject side.

In the present embodiment, because the insertion portion 11 is inserted into a bladder B as a predetermined organ through the urethra in the patient P, the illuminating light is irradiated into the bladder B and illuminates the inner surface of the bladder B.

As shown in FIG. 2, an objective lens 21 and a charge coupled device (abbreviated as "CCD") 22 that is disposed at an image forming position of the objective lens 21 are provided in the distal end portion 20 of the insertion portion 11, and an image pickup portion (or image pickup unit) 23 constituting image pickup means for picking up an image inside a predetermined organ is formed by the objective lens 21 and the CCD 22. The image pickup portion 23 picks up an image of a site that is illuminated by the illuminating light, and outputs an image pickup signal as an electrical signal obtained by photoelectric conversion.

Note that the CCD 22 includes a mosaic filter 22a that performs color separation in pixel units for the wavelength bands of, for example, red (R), green (G), and blue (B). Accordingly, for example, in the case of the normal light observation mode (WLI mode) which illuminates using white light, the CCD 22 outputs R, G, and B signals of a wide band that were subjected to color separation by the mosaic filter 22a, while in the case of the NBI mode, by picking up an image under illuminating light of the LEDs 16b and 16c, the CCD 22 outputs G and B signals of a narrow band (abbreviated as "Gn and Bn signals") that were subjected to color separation by the mosaic filter 22a.

The processor 5 has a CCD driving circuit (or CCD driving portion) 5c, and applies a CCD driving signal generated by the CCD driving circuit 5c to the CCD 22 via the signal wire 24 that is inserted through the inside of the endoscope 3. Upon application of the CCD driving signal thereto, the CCD 22 outputs an image pickup signal obtained by photoelectric conversion to the signal processing circuit (or signal processing portion) 5b provided in the processor 5 through the signal wire 24 that is inserted through the inside of the endoscope 3.

The signal processing circuit 5b generates a video signal (image signal) to display (an image picked up by the CCD 22) as an endoscopic image for displaying on the monitor 7. As also shown in FIG. 1, because the insertion portion 11 is inserted into the bladder B, the signal processing circuit 5b generates an image signal corresponding to an image picked up inside the bladder B. An image signal of a movie generated by the signal processing circuit 5b is outputted to the monitor 7, and the monitor 7 displays an endoscopic image (image pickup image) corresponding to the image signal of the movie. In the present specification, the terms "endoscopic image" and "image pickup image" have the same meaning.

The monitor 7 has a PinP (picture in picture) function, and together with an endoscopic image, displays a stereoscopic model image (referred to as "3D model image") in which the bladder B is simulated as described later and an insertion form image of the distal end side of the insertion portion 11.

Note that a configuration may also be adopted in which a PinP function of the monitor 7 is not utilized, and instead (an image signal of) an endoscopic image is inputted to the image processing apparatus 6, and image superimposing means (or an image superimposing portion) for superimposing an (image signal of) an insertion form image and (the image signal of) the endoscopic image is provided inside the image processing apparatus 6.

For example, a configuration may be adopted in which an endoscopic image generated by the signal processing circuit 5b inside the processor 5 is temporarily stored, for example, in a first predetermined area of a first frame memory (not shown) in a memory 33 inside the image processing apparatus 6, a 3D model image is temporarily stored in a second predetermined area of a second frame memory, and an insertion form image is temporarily stored in a third predetermined area of a third frame memory, and the three images are read out simultaneously from the three frame memories and superimposed by a display I/F 35, and the generated superimposition image is outputted to the monitor 7. In this case, (as shown in FIG. 2) the display I/F 35 has a function of an image superimposing portion (or image superimposing circuit) 35a.

Note that, even in a case where superimposing of an endoscopic image (by means of the PinP function of the monitor 7) is not to be performed, the image superimposing portion 35a performs image superimposition with respect to the 3D model image and the insertion form image to generate a superimposition image in which the insertion form image is superimposed on the 3D model image. Further, in the present embodiment a configuration is adopted so that, in a case where a release operation is performed, along with performing recording (storing) of an endoscopic image (image pickup image), processing is also performed that, in a size that is in accordance with a distance at which the endoscopic image (image pickup image) was picked up, pastes the endoscopic image (image pickup image) that is to be recorded (stored) on a 3D model image M1 at the position at which the endoscopic image (image pickup image) was picked up.

Figure 4:
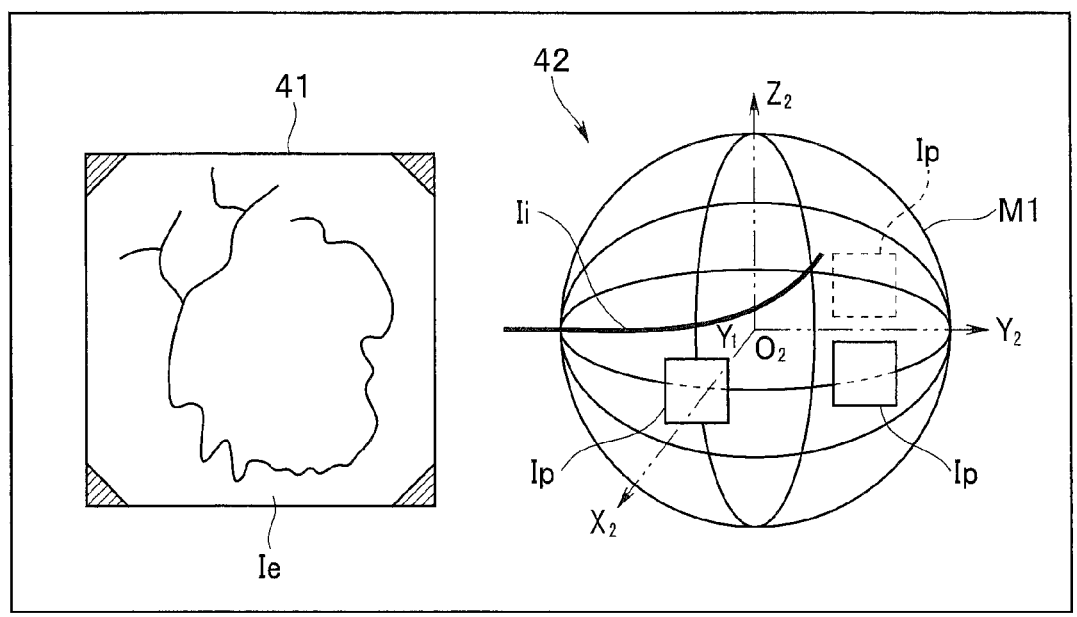
FIG. 4 is a view illustrating an endoscopic image and a 3D model image on which a pasting image is pasted that are displayed on a monitor.

Two images are displayed on the display screen of the monitor 7 as shown in FIG. 4 by means of the PinP function of the monitor 7 and the function of the image superimposing portion 35a. Specifically, an endoscopic image (image pickup image) Ie is displayed in a first area 41 as an endoscopic image display area (or real image display area, or image pickup image display area) on the left side of the display screen of the monitor 7, and an insertion form image Ii in which the form of the insertion portion 11 is superimposed on the 3D model image M1 is displayed in a second area 42 as a 3D image display area on the right side. Note that it can also be said that a composite image is displayed in the second area 42 as the 3D model image M1 on which the insertion form image Ii is superimposed.

Further, in a case where the surgeon as a user performs a release operation, a state is presented (displayed) in which an endoscopic image (image pickup image) of a size that is in accordance with the distance at which the image is picked up is pasted on the 3D model image M1 at a position at which the image is picked up (an endoscopic image (image pickup image) in a pasted state is referred to as "pasting image Ip").

Further, in the present embodiment, to enable detection of the three-dimensional position of the image pickup portion 23 that is disposed in the distal end portion 20 of the insertion portion 11 and a line of sight direction of the image pickup portion 23, as shown in an enlarged view in FIG. 1, a magnetic sensor 8 including two magnetic coils 8a that constitute two position sensors is disposed at a position in the vicinity of the CCD 22 in the distal end portion 20.

As shown in FIG. 2, the magnetic sensor 8 is connected to a position/direction detecting portion 34 inside the image processing apparatus 6 through a signal wire 8b that is inserted through the inside of the endoscope 3. By detecting the three-dimensional position of the two magnetic coils 8a, the position/direction detecting portion 34 calculates the position of the image pickup portion 23 and a line of sight direction in which the image pickup portion 23 picks up an image.

Specifically, the position/direction detecting portion (or position/direction detection circuit) 34 controls the driving circuit 37 that drives the magnetic field generating apparatus 9 to apply a driving signal for magnetic field generation to the magnetic field generating apparatus 9 from the driving circuit 37 through a signal wire 9a to cause the magnetic field generating apparatus 9 to generate a predetermined magnetic field, detects the magnetic field by means of the two magnetic coils 8a, acquires sensor information as the three-dimensional position of the two magnetic coils 8a based on the detection signal for the detected magnetic field, and generates three-dimensional position coordinates (x, y, z) of the image pickup portion 23 in the vicinity of the three-dimensional position of the two magnetic coils 8a and data regarding the line of sight direction thereof (that is, Eulerian angles $(\psi, \theta, \phi)$) as position/direction information in real time.

Note that, in a case where the position/direction detecting portion 34 acquires (detects) the three-dimensional position (x, y, z) of the two magnetic coils 8a as sensor information, as shown in FIG. 1, the position/direction detecting portion 34 generates (detects) the three-dimensional position on a first coordinate system $(X_0, Y_0, Z_0)$ that takes the vicinity of the magnetic field generating apparatus 9 as an origin $O_0$. Further, in a case where, as described later, the distal end portion 20 of the insertion portion 11 is inserted into the bladder B, coordinate conversion means (or a coordinate conversion portion) converts from the first coordinate system $(X_0, Y_0, Z_0)$ to a second coordinate system $(X_2, Y_2, Z_2)$ that takes as an origin $O_2$ the center of the 3D model image M1 in which the bladder B is simulated as a sphere, and performs pasting processing and the like.

The aforementioned position/direction detecting portion 34 has a function of an image pickup information acquisition portion (or an image pickup information acquisition circuit) 34a that forms image pickup information acquisition means for acquiring positional information and directional information from the magnetic sensor 8 and detecting positional information and line of sight information of the image pickup portion 23 as image pickup means.

Note that, since the magnetic sensor 8 is provided in the distal end portion 20, as well as having a function for calculating the position (information) and line of sight direction (information) of the image pickup portion 23, the position/direction detecting portion 34 also has a function for calculating the position (information) of the distal end portion 20 and the (longitudinal) direction (information) thereof. Consequently, the expression that the position/direction detecting portion 34 calculates (detects) the position and direction of the distal end portion 20 is also used.

The image pickup information acquisition portion 34a is not limited to a case of detecting positional information and line of sight information of the image pickup portion 23 as image pickup means, and a configuration may also be adopted in which the image pickup information acquisition portion 34a acquires only positional information of the image pickup portion 23 as image pickup means.

Further, in the present embodiment, the position and direction of the distal end portion 20 that are calculated by the position/direction detecting portion 34 are stored in chronological order at predetermined periods.

For example, the memory 33 stores the calculated position and direction of the distal end portion 20 in chronological order, and the position/direction detecting portion 34 refers to past information that is stored in chronological order in the memory 33, and calculates the insertion form of (primarily the distal end side of) the insertion portion 11 that is to be inserted into the bladder B as a predetermined organ by calculating the current position and direction of the distal end portion 20.

Therefore, the position/direction detecting portion 34 has a function of an insertion form information acquisition portion (or insertion form information acquisition circuit) 34b constituting insertion form information acquisition means for acquiring insertion form information in a case where the insertion portion 11 is inserted into the bladder B as the predetermined organ. Note that a configuration may also be adopted in which the image pickup information acquisition portion 34a is equipped with the function of the insertion form information acquisition portion 34b. Alternatively, a configuration may be adopted in which the insertion form information acquisition portion 34b is equipped with a function for acquiring positional information of the distal end portion 20 or the image pickup portion 23.

As shown in FIG. 2, a bending portion 25 including bending pieces 25a that bend freely in the upward/downward directions and left/right directions is provided in a hand-side end portion of the distal end portion 20 in the insertion portion 11. Note that although in FIG. 2 a simplified example is shown in which rivets 25b that enable bending are provided only, for example, in the upward/downward directions, in reality the rivets 25b are alternately provided in the upward/downward directions and left/right directions so as to enable bending.

Further, a wire 26 that, by pulling, causes the bending pieces 25a to bend in the upward/downward directions and left/right directions, respectively, is inserted through the inside of the insertion portion 11. A distal end of the wire 26 is fixed (not illustrated in the drawing) to a distal end member constituting the distal end portion 20, and a rear end of the wire 26 is wound around a pulley 27 that is disposed inside the operation portion 12.

A configuration is adopted so that, by performing an operation to rotate a bending knob 28 that is connected to the pulley 27, the surgeon can bend the bending portion 25 in an arbitrary direction among up/down and left/right. The image pickup direction of the image pickup portion 23 that is provided at the distal end of the bending portion 25 can be varied by bending the bending portion 25. By bending the bending portion 25 by a large amount, an inner wall surface on the side of a neck portion PR which serves as the entrance for insertion into the bladder B can be observed (an image thereof can be picked up).

As shown in FIG. 2, the image processing apparatus 6 includes: the CPU 31 that forms control means for controlling operations of each portion inside the image processing apparatus 6; an image capturing portion (or image capturing circuit) 32 that captures image signals outputted from the processor 5; a memory 33 constituting a recording portion that temporarily stores image signals inputted via the image capturing portion 32, temporarily stores various kinds of information, and records endoscopic images (image pickup images) in accordance with a release operation; and a position/direction detecting portion 34 that detects a position and a line of sight direction of the image pickup portion 23 disposed in the distal end portion 20 based on a detection signal of the magnetic sensor 8.

The image processing apparatus 6 also includes the display interface (display I/F) 35 that displays endoscopic images and the like on the monitor 7, an input portion (or user I/F) 36 for inputting various kinds of data, and the driving circuit 37 that drives the magnetic field generating apparatus 9. In the image processing apparatus 6, the CPU 31, . . . , display I/F 35 and input portion 36 are connected to each other through a data bus 38.

The memory 33 that constitutes a recording portion (storage portion) stores various kinds of processing programs to be executed by the CPU 31 and various kinds of data including data regarding the bladder B as the predetermined organ into which the insertion portion 11 is to be inserted. The CPU 31 generates a stereoscopic model (3D model) image M1 that simulates the bladder B into which the distal end portion 20 of the insertion portion 11 is to be inserted. Therefore, the CPU 31 has a function of a 3D model image generating portion (or 3D model image generating circuit) 31a that generates the 3D model image M1 of the bladder B as the predetermined organ. Since the bladder B is approximately spherical, for example, as shown on the right side in FIG. 4, the 3D model image generating portion 31a draws a 3D model image with a wire frame in which the bladder B is simulated with a spherical shape.

Further, when the distal end side of the insertion portion 11 is inserted into the bladder B, the CPU 31 generates a superimposition image for displaying the insertion form image Ii of the distal end side of the insertion portion 11 on the 3D model image M1 in a superimposed manner based on information regarding the position and direction of the distal end portion 20 obtained by the position/direction detecting portion 34. Therefore, the CPU 31 has a function of an insertion form image generating portion (or an insertion form image generating circuit) 31b that generates the insertion form image Ii (as a superimposed image on the 3D model image) in a case where the distal end side of the insertion portion 11 is inserted into the bladder 8.

Note that, the insertion form image generating portion 31b and the monitor 7 have a function of insertion form presentation means (or an insertion form presentation portion) or insertion form information presentation means (or an insertion form information presentation portion) for presenting (displaying) the generated insertion form image Ii on the monitor 7. Note that, in a narrow sense the monitor 7 can be regarded as having a function of insertion form presentation means or insertion form information presentation means.

Further, in a case where a release operation is performed, the CPU 31 records (stores) an endoscopic image (image pickup image) that is picked up by the image pickup portion 23 in the memory 33, and also has a function of an image pasting processing portion (or image pasting processing circuit) 31c that performs processing that pastes the endoscopic image (image pickup image) onto the 3D model image M1, and a function of a presentation processing portion (or a presentation processing circuit) 31d that performs image processing that presents (displays) the 3D model image M1 onto which the endoscopic image (image pickup image) is pasted as a pasting image Ip on the monitor 7 as display means.

Note that, although endoscopic image (image pickup image) generating means for generating an endoscopic image as an image pickup image that is picked up by the image pickup portion 23 is constituted by the signal processing circuit 5b of the processor 5, a configuration may also be adopted in which the image processing apparatus 6 is equipped with the function of the signal processing circuit 5b. Further, although in a narrow sense endoscopic image (image pickup image) presenting means for displaying (presenting) an endoscopic image (image pickup image) is constituted by the monitor 7, the endoscopic image (image pickup image) presenting means may also be defined so as to include the presentation processing portion 31d inside the image processing apparatus 6 that performs processing to display (present) an endoscopic image (image pickup image).

Further, although the main functions that the CPU 31 is equipped with are shown in FIG. 2, the functions of the CPU 31 are not limited to those shown in FIG. 2 and, for example, the presentation processing portion 31d may also be configured to also serve the functions of the 3D model image generating portion 31a, the insertion form image generating portion 31b, and the image pasting processing portion 31c. Further, as described later, a configuration may also be adopted in which the presentation processing portion 31d also serves a function of, for example, a planar model image generating portion (or expanded image generating portion) 31f.

By referring to the pasting image Ip of the endoscopic image (image pickup image) that is pasted on the 3D model image M1 and the insertion form image Ii on the monitor 7, the surgeon as the user of the endoscope system 1 can easily ascertain a site or the like at which an image is being picked up by the image pickup portion 23 inside the bladder B.

Further, in a case where the distal end portion 20 of the insertion portion 11 is inserted from the urethra into the bladder B, the CPU 31 has a function of an alignment processing portion (or alignment processing circuit) 31e that detects (calculates) the position and direction of the distal end portion 20 and the like in a first coordinate system ($X_0$, $Y_0$, $Z_0$) that takes the magnetic field generating apparatus 9 as an origin $O_0$, and performs alignment in a state in which the data is managed in alignment with a second coordinate system ($X_2$, $Y_2$, $Z_2$) that takes the center inside the bladder B as an origin $O_2$.

When performing alignment between the first coordinate system ($X_0$, $Y_0$, $Z_0$) and the second coordinate system ($X_2$, $Y_2$, $Z_2$), although a mediating coordinate system ($X_1$, $Y_1$, $Z_1$) is used that, for example, takes as an origin $O_1$ a position of the neck portion PR (see enlarged view of FIG. 1) that is a position at the terminus of the urethra and is a starting point for insertion into the bladder B, alignment may also be performed without using the coordinate system ($X_1$, $Y_1$, $Z_1$).

The alignment processing portion 31e also serves a function of coordinate conversion means or a coordinate conversion processing portion (or coordinate conversion processing circuit) that performs coordinate conversion from the first coordinate system ($X_0$, $Y_0$, $Z_0$) that takes the magnetic field generating apparatus 9 as the origin $O_0$ to the second coordinate system ($X_2$, $Y_2$, $Z_2$) that takes the center inside the bladder B as the origin $O_2$ (via the coordinate system ($X_1$, $Y_1$, $Z_1$) that takes as the origin $O_1$ the position of the neck portion PR that is a position at the terminus of the urethra and is a starting point for insertion into the bladder B).

FIG. 1 illustrates the first coordinate system ($X_0$, $Y_0$, $Z_0$) that takes the magnetic field generating apparatus 9 as the origin $O_0$ and, in an enlarged view in which the bladder 8 is schematically enlarged as the stereoscopic model image (3D model image) M1, also illustrates the coordinate system ($X_1$, $Y_1$, $Z_1$) that takes as the origin $O_1$ the position of the neck portion PR that is a position at the terminus of the urethra and is a starting point for insertion into the bladder B, and the second coordinate system $(X_2, Y_2, Z_0)$ that is shifted by a predetermined distance in a $Y_1$ direction ($Y_2$ direction) from the coordinate system $(X_1, Y_1, Z_1)$ and set.

In the enlarged view, a neck-portion opposing site of the spherical 3D model image M1 that simulates the bladder B that is a site that is opposite to the neck portion PR is denoted by reference characters PT. The origin $O_2$ of the second coordinate system $(X_2, Y_2, Z_0)$ is the position of the middle point of a line segment that links the neck portion PR and the opposing site PT that opposes the neck portion PR. Further, the second coordinate system $(X_2, Y_2, Z_0)$ is set so that a left wall side in the bladder B is the $X_2$ direction, a right wall side is a $-X_2$ direction, an abdominal part (anterior wall) side of the patient P is the $Z_2$ direction, and a back (posterior wall) side of the patient P is a $-Z_2$ direction.

Note that, a planar model image M2 (see FIG. 9, FIG. 11 and the like) that is described later is an image that is expanded or projected along a plane including $X_2$ and $Y_2$ in the enlarged view.

When a release operation is performed by the surgeon, the CPU 31 records an endoscopic image (or image pickup image) from the processor 5 in the memory 33. That is, the memory 33 has a function of an endoscopic image recording portion (or image pickup image recording portion) 33a that records an endoscopic image (or image pickup image). The memory 33 also has a function of a pasting image recording portion 33b that, in a case where a release operation is performed, records a pasting image Ip that is to be pasted on the 3D model image M1.

Note that, in the present embodiment an electronic endoscope is used that has a configuration in which the image pickup portion 23 constituting image pickup means is mounted in the distal end portion 20 of the insertion portion 11, and the magnetic sensor 8 that detects the three-dimensional position and the like of the image pickup portion 23 (or distal end portion 20) is provided in the vicinity of the image pickup portion 23.

In this regard, a configuration may also be adopted in which a distal end face of an image guide that is inserted through the inside of the insertion portion 11 is disposed at an image forming position of the objective lens 21, and an optical image that is transmitted to a rear end face of the image guide is picked up by a CCD or the like. Further, image transmission means constituted by a relay optical system may be used instead of an image guide. Note that, although in FIG. 2 an example is illustrated in which the 3D model image generating portion 31a, the insertion form image generating portion 31b, the image pasting processing portion 31c, the presentation processing portion 31d and the alignment processing portion 31e are constituted by the CPU 31, these portions may be constituted using an electronic device or the like, or may be constituted using an FPGA or the like. The same applies with respect to FIG. 8 that is described later.

In the case of picking up an image using the image transmission means that is inserted through the inside of the insertion portion 11 in this way, the magnetic sensor 8 detects the position and the like of the distal end portion 20 or the objective lens 21 that is disposed in the distal end portion 20. Note that, in a case where the insertion portion 11 is a rigid insertion portion, the magnetic sensor 8 need not be disposed in the distal end portion 20 of the insertion portion 11 and may be provided at a position that is separated by a predetermined distance from the distal end portion 20, in other words, the magnetic sensor 8 may be provided at a position such that the magnetic sensor 8 maintains a predetermined positional relationship with the distal end portion 20. Further, the magnetic sensor 8 may also be provided in a member that is connected so as to maintain a predetermined positional relationship with the distal end portion 20.

The endoscope system 1 of the present embodiment configured in this manner is characterized by including: the insertion portion 11 to be inserted into a subject; the endoscope 3 having the image pickup portion 23 constituting image pickup means for picking up an image inside the subject; the insertion form information acquisition portion 34b constituting insertion form information acquisition means for acquiring positional information and directional information from the magnetic sensor 8 provided in the vicinity of the image pickup means or in a member that is connected so as to maintain a predetermined positional relationship with the image pickup means, and acquiring positional information of the image pickup means and insertion form information with respect to the form of the insertion portion 11 that is inserted; the image pasting processing portion 31c constituting image pasting means for pasting, based on positional information of the image pickup means, an image pickup image that is picked up by the image pickup means as the pasting image Ip on the stereoscopic model image M1 that simulates the bladder B that forms the predetermined organ inside the subject; and the monitor 7 constituting insertion form information presentation means for associating the insertion form information acquired by the insertion form information acquisition means with the stereoscopic model image M1 that is pasted by the image pasting means and presenting the associated information and image.

Figure 5:
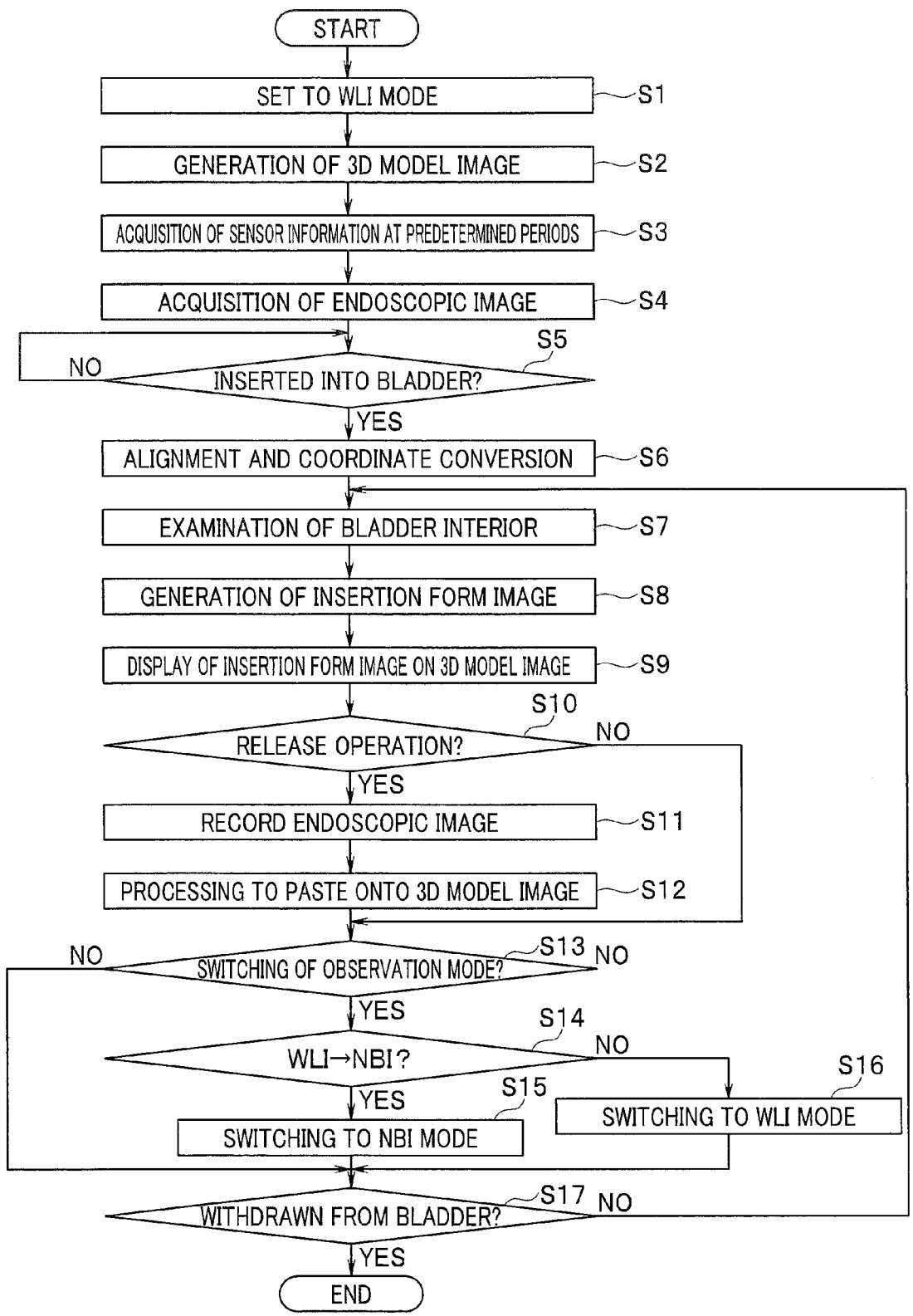
FIG. 5 is a flowchart illustrating a processing example of the first embodiment.

Next, operations of the present embodiment will be described referring to FIG. 5. FIG. 5 illustrates a processing example in a case of performing endoscopy inside the bladder B according to the present embodiment.

As shown in FIG. 1, the endoscope 3 is connected to the light source apparatus 4 and the processor 5 and the like, and the distal end portion 20 of the insertion portion 11 of the endoscope 3 is inserted into the bladder B via the urethra of the patient P.

In this case, as shown in step S1 of FIG. 5, for example, the surgeon selects the normal light mode (WLI mode) in which the light source apparatus 4 outputs the white light W as the illuminating light. Note that, a configuration may also be adopted in which the endoscope system 1 is set to start in the nominal light mode when the endoscope system 1 starts when the power is turned on.

Further, as shown in step S2, the surgeon, for example, performs an input operation from the input portion 36 to specify the bladder B as a predetermined organ that is the examination object, and in accordance with this input operation the 3D model image generating portion 31a of the CPU 31 generates the 3D model image M1 of the bladder B. The CPU 31 also acquires information regarding the focal distance and view angle and the like of the image pickup system of the image pickup portion 23.

As shown in step S3, the position/direction detecting portion 34 acquires sensor information of the magnetic sensor 8 that is provided in the distal end portion 20 of the insertion portion 11 at predetermined periods, and starts to generate (calculate) positional and directional information of the distal end portion 20 or the image pickup portion 23.

Further, as shown in step S4, in synchrony with the periods at which the sensor information is acquired, the image processing apparatus 6 starts to acquire endoscopic images as image pickup images that are picked up by the image pickup portion 23, via the image capturing portion 32.

As shown in step S5, the surgeon observes the endoscopic image and determines whether or not the distal end portion 20 of the insertion portion 11 is inserted inside the bladder B. Note that, a configuration may also be adopted so as to determine whether or not the distal end portion 20 of the insertion portion 11 is inserted inside the bladder B by means of image processing by the image processing apparatus 6. As shown in the subsequent step S6, the alignment processing portion 31e sets the distal end portion 20 of the insertion portion 11 at a reference position such as the neck portion PR inside the bladder B and performs alignment between the first coordinate system ($X_0$, $Y_0$, $Z_0$) and the second coordinate system ($X_2$, $Y_2$, $Z_2$) that takes the center position of the 3D model image as the origin $O_2$, and also determines a conversion matrix or the like for converting from the first coordinate system ($X_0$, $Y_0$, $Z_0$) to the second coordinate system ($X_2$, $Y_2$, $Z_2$) and converts the positional and directional information acquired in the first coordinate system ($X_0$, $Y_0$, $Z_0$) to positional and directional information in the second coordinate system ($X_2$, $Y_2$, $Z_2$).

As shown in step S7, the surgeon examines the inner surface of the bladder B while observing an endoscopic image of the inside of the bladder B. As described above, the position/direction detecting portion 34 generates information regarding the position and direction of the distal end portion 20 at predetermined periods, and the insertion form information acquisition portion 34b acquires information regarding the insertion form of the insertion portion 11 inside the bladder B.

Further, as shown in step S8, the insertion form image generating portion 31b of the CPU 31 generates the insertion form image Ii of the insertion portion 11 inside the bladder B. As shown in step S9, the insertion form image Ii is superimposed on the 3D model image M1 that simulates the bladder B and the resulting image is displayed (presented) on the monitor 7. By displaying the insertion form image Ii, the surgeon can easily ascertain the insertion form of the distal end side of the insertion portion 11 inside the bladder B, to thereby facilitate performance of a bending operation in a case where the surgeon bends the bending portion 25 to change the insertion form as well as operations such as an operation to change the field of view direction.

Note that, as shown in FIG. 4, a configuration may also be adopted so as to display the insertion form image Ii that includes a portion showing the form of the insertion portion 11 in a region on an outer side of the spherical 3D model image M1 that simulates the bladder B.

The surgeon examines the inner surface of the bladder B while observing the endoscopic image of the inside of the bladder B, and performs a release operation when examining a lesion site or a site that the surgeon wishes to record. As shown in step S10, the CPU 31 monitors to detect the performance of a release operation. Upon a release operation being performed, as shown in step S11, the CPU 31 records the endoscopic image obtained at the timing that the release operation is performed in the memory 33.

Further, as shown in step S12, the image pasting processing portion 31c of the CPU 31 performs processing that pastes the endoscopic image obtained at the timing that the release operation was performed (that is, the endoscopic image to be recorded) as the pasting image Ip in an image pickup range corresponding to the view angle at which the image was picked up, at the corresponding position on the 3D model image M1. Note that, in a case where a release operation is not performed, the operation moves to the processing in step S13 without performing the processing in steps S11 and S12.

Figure 6:
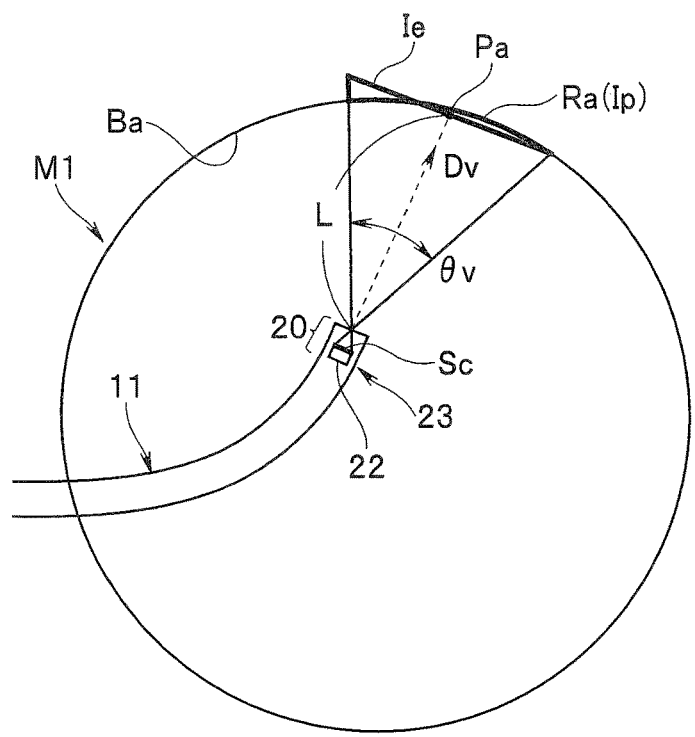
FIG. 6 is an explanatory view for describing a case where an endoscopic image is pasted on a 3D model image.

FIG. 6 illustrates the manner in which, when a release operation is performed, the pasting image Ip is pasted at a corresponding position and in a corresponding range on the 3D model image M1.

As shown in FIG. 6, an optical image within the range of a view angle θv on an (inner surface of the 3D model image M1 that simulates an) inner surface Ba of the bladder B is formed on an image pickup surface Sc of the CCD 22 forming the image pickup portion 23 that is provided in the distal end portion 20 of the insertion portion 11, and an endoscopic image corresponding to the optical image is displayed on the display screen of the monitor 7.

In FIG. 6, an image on a plane that is orthogonal to a line of sight direction Dv of the image pickup portion 23 at a point Pa that intersects with the inner surface Ba in the line of sight direction Dv, that is, an image corresponding to the optical image on the image pickup surface Sc, is shown as an endoscopic image Ie. In this case, an image pickup range Ra (indicated by a thick line) of the inner surface Ba in which an image is picked up and the range of the endoscopic image Ie are substantially matching. However, in general, the two ranges differ.

In other words, the image pickup range (range of the endoscopic image Ie) Ra in which an image is picked up changes according to a distance L along the line of sight direction Dv from the distal end portion 20 to the inner surface Ba of the bladder B. For example, if the distance L decreases, the image pickup range Ra in which an image is picked up decreases, while if the distance L increases, the image pickup range Ra increases. Note that, the image pickup range Ra also varies depending on the size of the view angle θv of the image pickup portion 23.

In the present embodiment, the size of the pasting image Ip that is pasted on the 3D model image M1 is changed according to the distance L (from the image pickup portion 23 of the distal end portion 20) to the inner surface Ba of the sphere that simulates the bladder B. Specifically, taking a point at which a straight line along the line of sight direction Dv from the image pickup portion 23 of the distal end portion 20 intersects with the inner surface Ba of the sphere as a center, the image pasting processing portion 31c of the CPU 31 generates a pasting image Ip by pasting on the 3D model image M1 an endoscopic image of a size that approximately matches the image pickup range Ra in which the image was picked up. In FIG. 6, the pasting image Ip is pasted at a portion of the image pickup range Ra that is a curved surface indicated by a thick curved line (denoted by reference characters "Ra(Ip)").

Therefore, the image pasting processing portion 31c that forms the image pasting means simulates the bladder B as the predetermined organ, and in a size that approximately matches the range in which the relevant image is picked up, pastes an image pickup image (as an endoscopic image) that is picked up by the image pickup portion 23 in a state in which the distal end portion 20 of the insertion portion 11 is inserted inside the bladder B as the predetermined organ at a position at which the image is picked up by the image pickup portion 23 on the spherical stereoscopic model image M1 that is drawn with a wire frame.

Thus, the pasting image Ip as shown in FIG. 4 is displayed. FIG. 4 shows a state in which two pasting images Ip are displayed (presented). By looking at the insertion form image Ii and the pasted pasting image Ip that are displayed on the 3D model image M1, the surgeon can easily ascertain the state that is actually being observed (examined) inside the bladder B, and can also easily ascertain the position and range of the endoscopic image that was recorded by the release operation.

Note that, although the external form of the pasting image Ip is shown as a quadrangle that is close to a square in FIG. 4, as shown on the left side in FIG. 4, a configuration may also be adopted in which the pasting image Ip is shown as an octagon in which four corners are cut off (the cut-off portions are indicated by diagonal lines). Alternatively, a configuration may be adopted in which the endoscopic image shown on the left side in FIG. 4 is shown as a quadrangle (in which four corners are not cut off).

Furthermore, the shape of the endoscopic image may be changed by also taking into consideration the positional relation between the line of sight direction Dv and the inner surface Ba of the bladder B, and not just the distance L, and pasted on the spherical stereoscopic model image M1.

As shown in step S13 in FIG. 5, the CPU 31 monitors whether or not a switching operation is performed to switch the observation mode. If a switching operation is not performed, the CPU 31 moves to the processing in step S17. In contrast, if a switching operation is performed, as shown in step S14, the CPU 31 determines whether or not the switching operation is from the WLI to the NBI mode.

If the result determined in step S14 is that the switching operation is from the WLI to the NBI mode, as shown in the next step S15, the control circuit 5a of the processor 5 switches to the NBI mode. In this case, the control circuit 5a controls so that the light source apparatus 4 outputs Bn light and Gn light, the signal processing circuit 5b performs signal processing corresponding to the NBI mode, and the signal processing circuit 5b outputs an endoscopic image obtained in the NBI mode to the image processing apparatus 6 side. Further, the control circuit 5a sends information indicating that the observation mode is switched to the NBI mode to the CPU 31, and the CPU 31 ascertains that the state is one in which observation has been switched to the NBI mode. By switching to the NBI mode, the surgeon can observe in more detail the running state and the like of blood vessels near the surface of the bladder B.

In a case where the result determined in step S14 is that the switching operation is not from the WLI to the NBI mode, as shown in step S16, the control circuit 5a of the processor 5 switches from the NBI mode to the WLI mode. In this case, the control circuit 5a controls so that the light source apparatus 4 outputs the white light W, the signal processing circuit 5b performs signal processing corresponding to the WLI observation mode, and the signal processing circuit 5b outputs an endoscopic image obtained in the WLI mode to the image processing apparatus 6 side. Further, the control circuit 5a sends information indicating that the observation mode is switched to the WLI mode to the CPU 31, and the CPU 31 ascertains that the state is one in which observation has been switched to the WLI mode.

In steps S15 and S16, the spherical stereoscopic model image M1 is switched in accordance with the observation mode.

As shown in step S17, the CPU 31 determines whether or not the surgeon has withdrawn the insertion portion 11 from inside the bladder B and performed an operation to instruct that endoscopy is to be ended. If an operation to instruct that endoscopy is to be ended is not performed, the operation returns to the processing in step S7 to repeat the processing from steps S7 to S17. In contrast, if an operation to instruct that endoscopy is to be ended is performed, the CPU 31 ends the processing in FIG. 5.

According to the first embodiment that operates in this way, the stereoscopic model image (3D model image) that simulates the predetermined organ and the image pickup image (or endoscopic image) are presented to facilitate ascertainment of the relation with the insertion form, and thus performance of examination or the like of a site such as the lesion site which the surgeon is attempting to examine can be facilitated.

Further, in the present embodiment, since a configuration is adopted so as to paste the pasting image Ip onto the 3D model image in a manner that takes into consideration three-dimensional positional and directional information in a case where an image of the inner surface of the bladder B is picked up, the positional relation with a site such as a lesion site that the surgeon wants to attempt to examine can be easily ascertained, and smooth performance of examination or treatment inside the bladder or the like can be facilitated.

Figure 7:
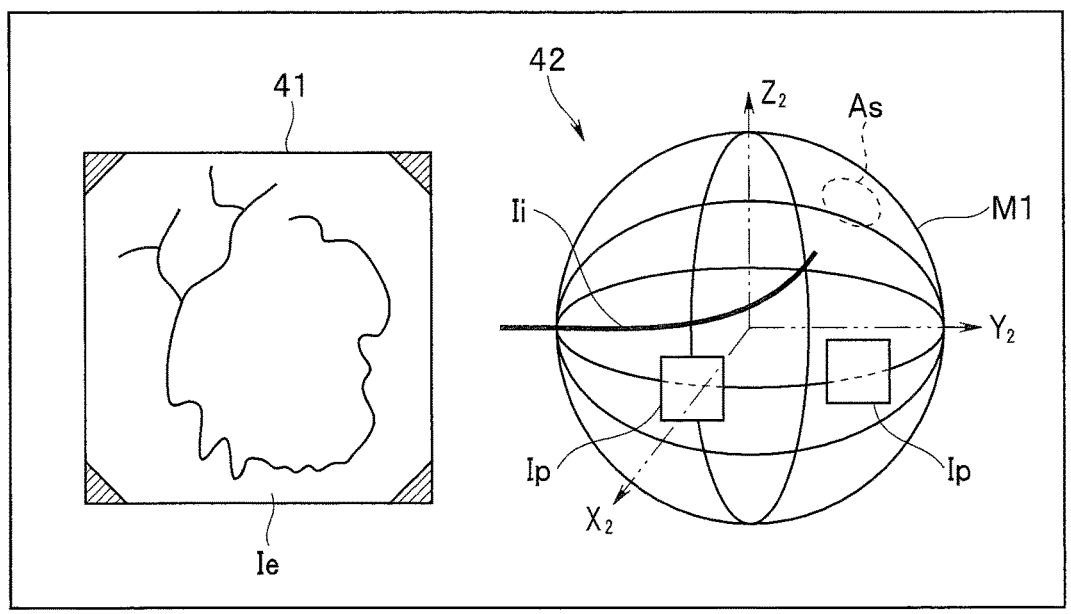
FIG. 7 is a view illustrating the manner in which a current view angle is displayed on a 3D model image.

In the present embodiment, as shown in FIG. 7, a configuration may also be adopted in which the field of view range (or image pickup range) As (Ra) that the image pickup portion 23 of the distal end portion 20 is currently picking up an image of is displayed (presented) on the 3D model image M1. Note that, FIG. 7 shows an example of the display (presentation) on the display screen of the monitor.

For example, the presentation processing portion 31d of the CPU 31 refers to information of the image pickup information acquisition portion 34a and the like to calculate the inner surface of the bladder B that the image pickup portion 23 is currently picking up an image of, in other words, the field of view range As or image pickup range Ra on the 3D model image M1, and displays (presents) the calculated field of view range As or image pickup range Ra using, for example, a dashed line, a thin line, a thick line or the like on the 3D model image M1.

Since the image pickup portion 23 that is mounted in the distal end portion 20 of the insertion portion 11 of the endoscope 3 that is actually used will generally differ according to the kind of endoscope and the like, the field of view range As thereof will also differ. In the present embodiment, information regarding the field of view range As of the image pickup portion 23 is acquired from the ROM 19.

Note that, in the case of an endoscope that does not have the ROM 19, or when information regarding the field of view range As cannot be acquired, the information regarding the field of view range As may be inputted into the CPU 31 from a keyboard or the like constituting the input portion 36.

In a case where the surgeon performs an operation to pick up an image of the inner surface of the bladder B and examines whether or not the site is a lesioned part, or assesses whether or not a biopsy or treatment is necessary, because the field of view range As in which an image is currently being picked up is displayed (presented) on the 3D model image M1, the surgeon can always ascertain which position on the 3D model image M1 an image is being picked up at. Further, since the size of the region in the field of view range As can also be ascertained, the surgeon can also ascertain whether or not the distance to the inner surface of the bladder B is within an appropriate range. Note that, although in FIG. 7 the field of view range As is shown as a circle, the field of view range As may be displayed as a shape that is in accordance with the shape of the image pickup area of the CCD 22, for example, a square. A configuration may also be adopted so as to display the field of view range As in a shape that is in accordance with the spherical shape of the 3D model image M1 that is displayed on the monitor 7.

Note that, although in the above described description an endoscopic image that is obtained when a release operation is performed is described as the pasting image Ip to be pasted on the 3D model image M1, the present invention is not limited to the aforementioned endoscopic image, and a configuration may also be adopted in which an image corresponding to the relevant endoscopic image is pasted. For example, a configuration may be adopted that enables the surgeon to select between an endoscopic image obtained when a release operation is performed and a schematic image of a size in which the relevant endoscopic image is to be pasted.

In addition, as shown in FIG. 4, in a case where the 3D model image M1 that simulates the predetermined organ is schematically displayed with a wire frame, with respect to a hemisphere on the $X_2$ side (front side) that is obtained by dividing along a plane including the origin $O_2$, $Y_2$ and $Z_2$ of the second coordinate system, in a case where an endoscopic image obtained by picking up an image from inside (the 3D model image M1 that simulates) the predetermined organ is pasted as the pasting image Ip, the surgeon observes from the outside (not the inside) of the hemisphere. In contrast, with respect to the other hemisphere that is the opposite side to the hemisphere on the $X_2$ side (front side), in a case where an endoscopic image is pasted as the pasting image Ip, the surgeon can observe from the inside of the 3D model image M1 through the hemisphere on the front side.

In other words, when pasting an endoscopic image (image pickup image) that is obtained by picking up an image of the inner surface of the bladder B that simulates the predetermined organ by means of the image pickup means as the pasting image Ip on the approximately spherical surface of the 3D model image M1, the 3D model image M1 has a first pasting face (specifically, the aforementioned other face) on which the endoscopic image (image pickup image) is pasted so that the user such as a surgeon can observe the image surface side of the pasting image Ip, and a second pasting face (specifically, the surface on the aforementioned front side) on which the endoscopic image (image pickup image) is pasted so that the user such as a surgeon can observe the rear surface side of the image surface of the pasting image.

Therefore, a configuration may also be adopted so that, in a case where a release operation is performed and the endoscopic image to be pasted is pasted and presented (displayed) as the pasting image Ip at a corresponding position on the 3D model image M1, in the hemisphere on the $X_2$ side (front side), an image in which the left/right directions (in the second coordinate system) of the relevant endoscopic image are inverted is pasted as the pasting image Ip, while in the other hemisphere (to realize a state in which the inner surface of the 3D model image M1 is observed) an image in which the left/right directions (in the second coordinate system) of the relevant endoscopic image are not inverted is pasted as the pasting image Ip. In FIG. 4, the pasting image Ip on the other hemisphere is indicated by a dashed line. Thus, the image pasting processing portion 31c constituting the image pasting means may also be configured to, with respect to the aforementioned second pasting face, paste and present an image in which the left/right directions of the endoscopic image (image pickup image) are inverted as the pasting image Ip.

By adopting such a configuration, in a case where an endoscopic image of the inner surface of a predetermined organ that the surgeon records by performing a release operation is pasted at a position and in an image pickup range at which the image was picked up (recorded) on the spherical surface of the predetermined organ and the state is one in which the surgeon can observe the endoscopic image as it is at the time of pasting, the endoscopic image is pasted as the pasting image Ip without inverting the left/right directions, while in a case where the state is one in which the surgeon is observing from the rear face (back face) side of the endoscopic image at the time of pasting, an endoscopic image in which the left/right directions that correspond to the rear face of the endoscopic image at the time of pasting are inverted is presented as the pasting image Ip. Hence, ascertainment by the surgeon of the state of the inner surface of the predetermined organ from the pasting image Ip that is pasted on the 3D model image M1 is facilitated.

Accordingly, even in a case where the surgeon observes an endoscopic image, obtained by a release operation, of the inner surface of the predetermined organ from outside the spherical surface of the corresponding 3D model image M1, the observation state of the bladder B can be easily ascertained from the endoscopic image, and thus performance of endoscopy or diagnosis or the like is facilitated.

Further, although in the above description a case is described in which an endoscopic image or the like is pasted on the 3D model image M1 only in a case where a release operation is performed, a configuration may also be adopted that allows the surgeon to set conditions for pasting and presenting a pasting image from the input portion 36.

For example, apart from when the surgeon performs a release operation, a configuration may be adopted so as to also paste an endoscopic image on the 3D model image M1 and display (present) the endoscopic image as the pasting image Ip at time intervals that are specified by the surgeon. A configuration may also be adopted in which an instruction switch is provided for issuing a paste instruction, and when the instruction switch is operated, an endoscopic image or the like that is obtained at the timing at which the instruction switch is operated is pasted.

Second Embodiment

Figure 8:
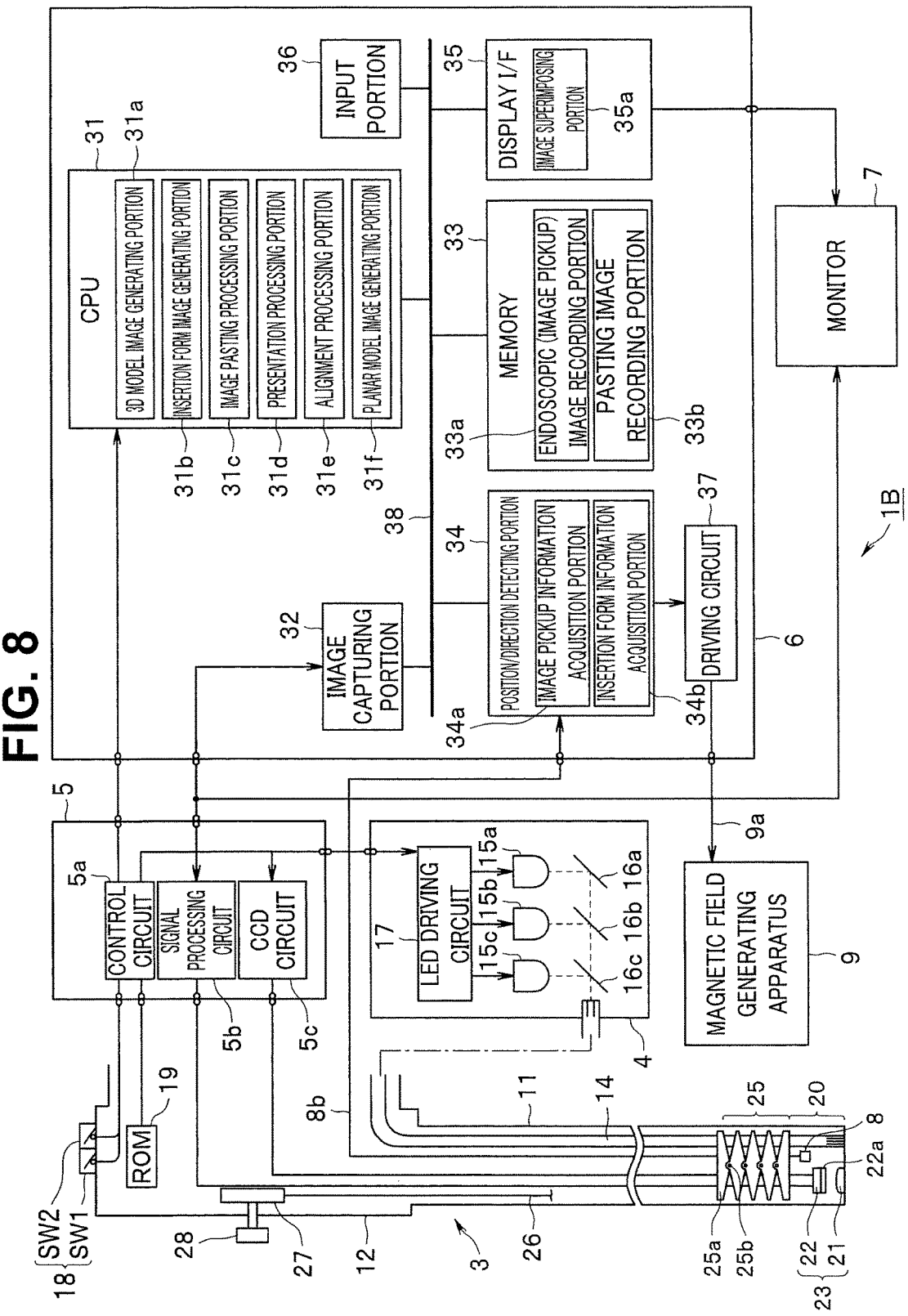
FIG. 8 is a view illustrating the internal configuration of an endoscope system according to a second embodiment of the present invention.

Next, a second embodiment of the present invention will be described. FIG. 8 illustrates an endoscope system 1B of the present embodiment. Relative to the endoscope system 1 illustrated in FIG. 2, in the endoscope system 1B in FIG. 8 the CPU 31 further includes a function of a planar model image generating portion (or an expanded image generating portion) 31f that is constituted by a planar model image generating circuit (or an expanded image generating circuit) that generates a planar model image M2 in which a stereoscopic model image corresponding to the bladder B as a predetermined organ is planarly expanded, and the planar model image generating portion (or expanded image generating portion) 31f or the image pasting processing portion 31c pastes an image pickup image (endoscopic image) as a pasting image at a corresponding position on the planar model image M2 based on positional information of the image pickup means and displays (presents) the planar model image M2 on which the pasting image has been pasted on the display screen of the monitor 7.

Figure 9:
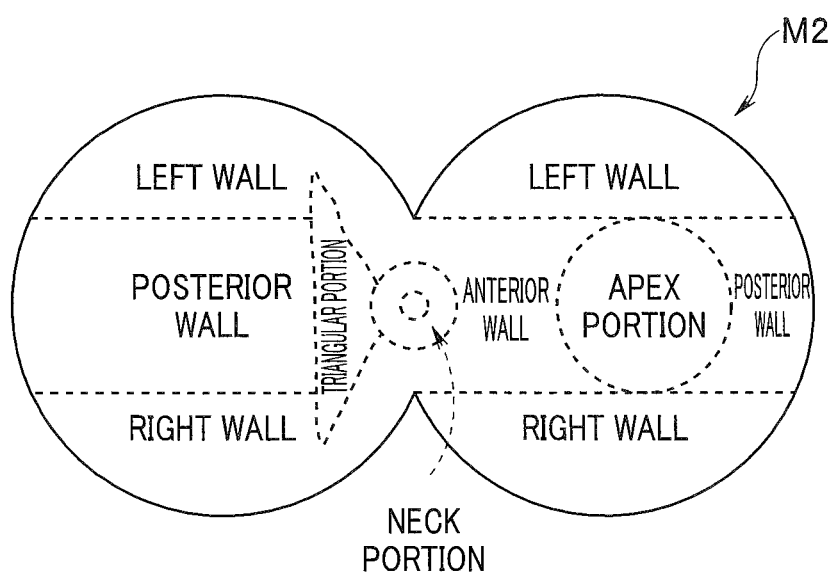
FIG. 9 is a view illustrating respective regions of an inner surface of a bladder that is represented with a planar model image.

The planar model image M2 in the present embodiment is a planar (2D) image in which the substantially spherical bladder B is expanded along a plane that passes through the neck portion PR and the opposing site PT that opposes the neck portion PR, as well as the left wall and right wall. The relation between positions (regions) on the planar model image M2 and regions of respective portions on the substantially spherical inner surface of the bladder B is as shown in FIG. 9.

Thus, the present embodiment includes expanded image generating means (or planar model image generating means) for, based on positional information of the image pickup means, pasting and presenting an image pickup image on the planar model image M2 in which a stereoscopic model image corresponding to a predetermined organ is planarly expanded. In other words, in the present embodiment, the planar model image generating portion 31f includes the expanded image generating means (or planar model image generating means) for, based on positional information of the image pickup means, pasting and presenting an image pickup image in position on the planar model image M2 in which a stereoscopic model image corresponding to a predetermined organ is planarly expanded.

Further, according to the present embodiment, in a case where a release operation is performed, a pasting image is pasted at a position at which the relevant image was picked up by the image pickup portion 23 on the planar model image M2, and at such time, a pasting image that is later in time is pasted so as to be on an upper side of an older pasting image. The remaining configuration is the same as the configuration of the first embodiment.

Figure 10:
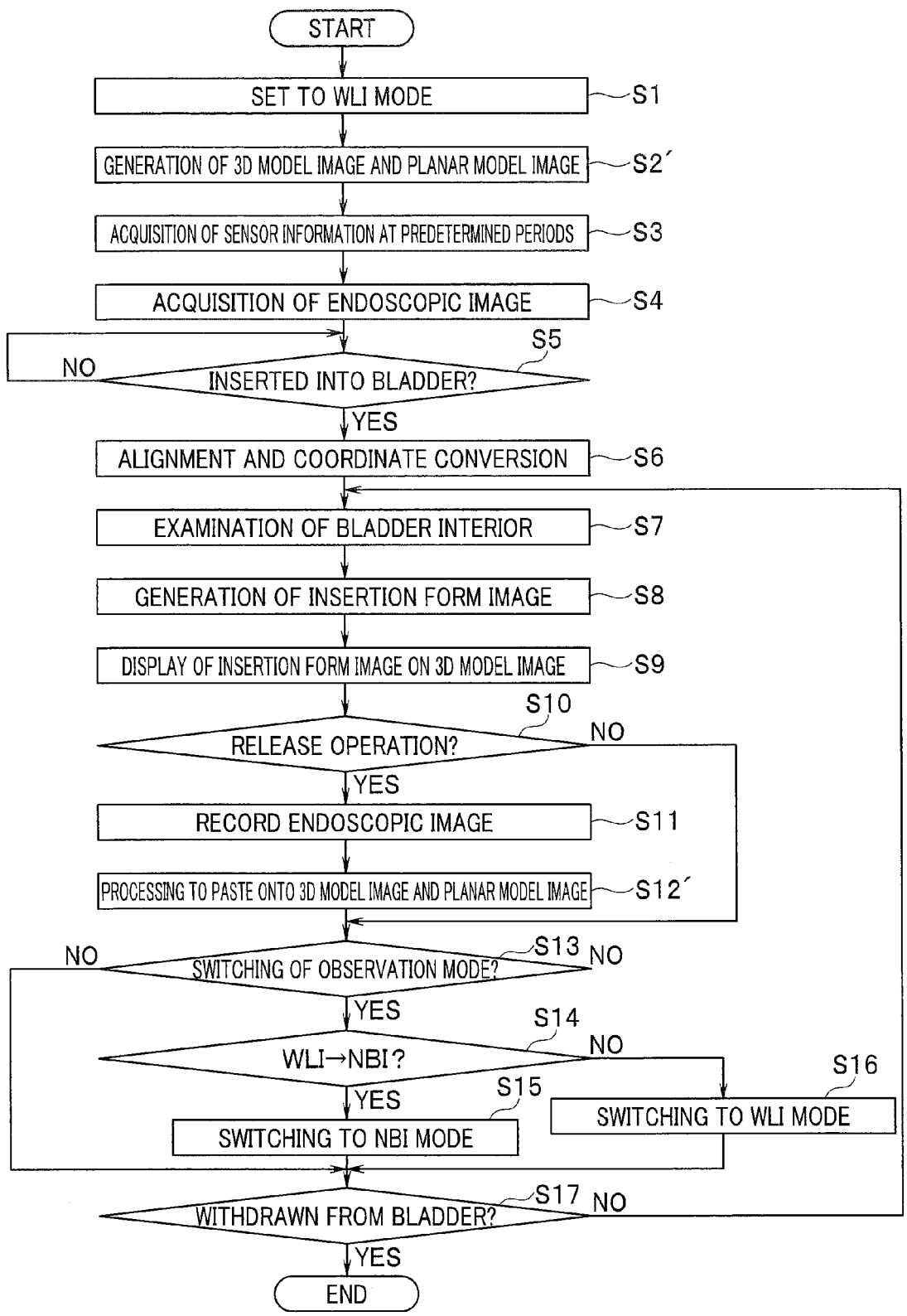
FIG. 10 is a flowchart illustrating a processing example of the second embodiment.

The operations of the present embodiment are as illustrated in FIG. 10 that is similar to FIG. 5 that relates to the first embodiment. The processing in FIG. 10 is similar to the processing in FIG. 5, except that the processing in step S2 and step S12 in FIG. 5 is replaced in FIG. 10 by the processing in step S2' and step S12', respectively.

In step S2', the 3D model image generating portion 31a of the CPU 31 generates the 3D model image M1, and the planar model image generating portion 31f generates the planar model image M2.

Further, in step S12', the image pasting processing portion 31c of the CPU 31 pastes the endoscopic image (image pickup image) that is obtained when a release operation is performed as a pasting image at corresponding positions on the 3D model image M1 and the planar model image M2, respectively. The remaining processing is the same as the processing described in FIG. 5.

Figure 11:
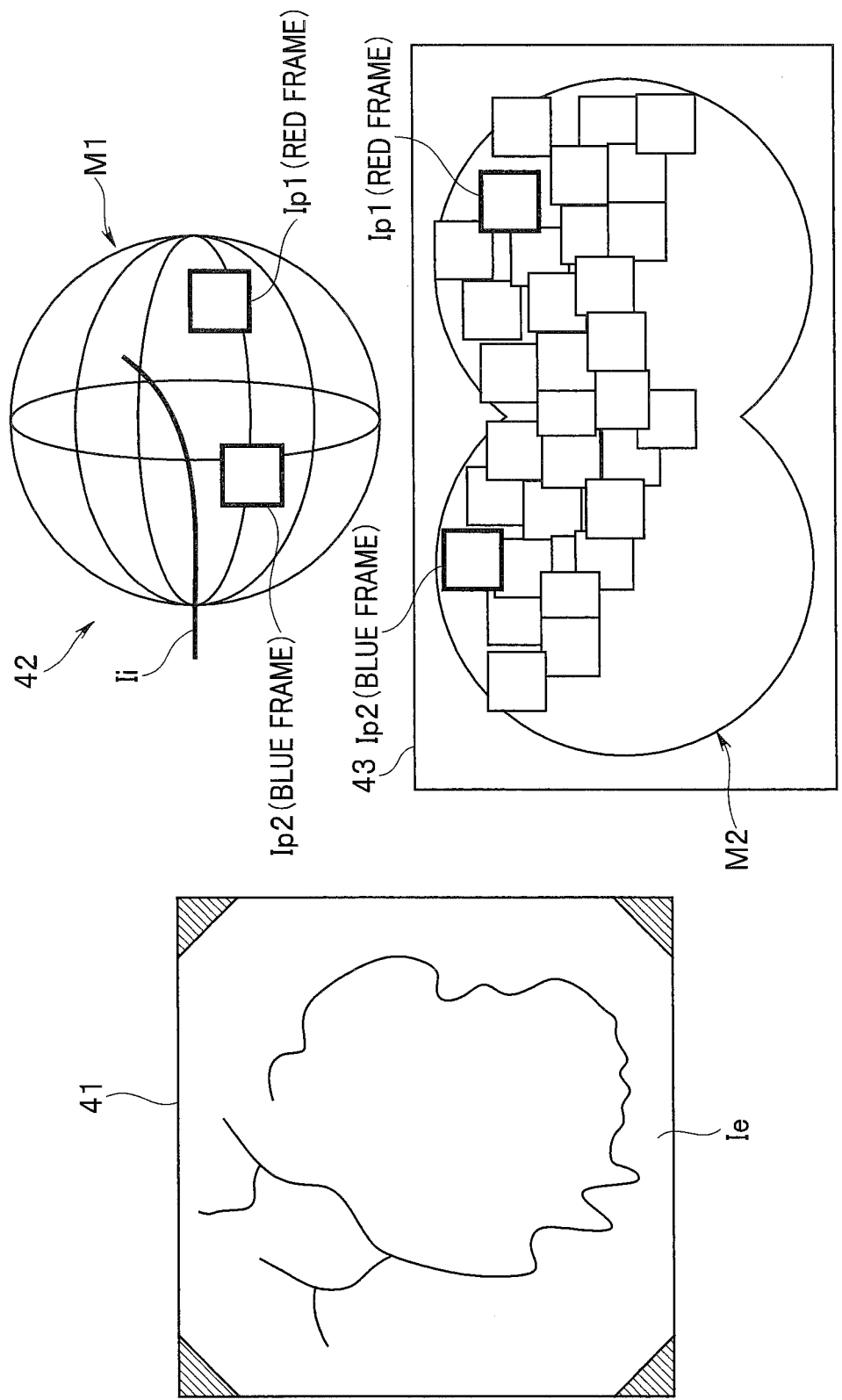
FIG. 11 is a view illustrating the manner in which a pasting image is displayed on a 3D model image and a planar model image.

FIG. 11 illustrates a display example in which the 3D model image M1 and the planar model image M2 on which pasting images are pasted are displayed on the display screen of the monitor 7. In the display example in FIG. 11, a first area 41 is provided on the left side of the display screen, a second area 42 is provided on an upper section side on the right side of the first area 41, and a third area 43 as a planar model image display area is provided on a lower section side on the right side of the first area 41. Note that, the present invention is not limited to a case of displaying (presenting) the endoscopic image, 3D model image M1 and planar model image M2 in the manner of the arrangement illustrated in FIG. 11, and for example, the arrangement of the second area 42 and the third area 43 may be reversed.

In the present embodiment, when pasting an endoscopic image obtained at the time of a release operation on the 3D model image M1 and the planar model image M2, a frame of the same color is added to the same pasting image and the frame and pasting image are displayed (presented).

For example, in a case where the time of a release operation is t1, a pasting image Ip1 to which a, for example, red frame is added is pasted and displayed at a corresponding position on the 3D model image M1, and with respect to the planar model image M2 also, the pasting image Ip1 is pasted and displayed with a red frame at a corresponding position on the planar model image M2.

Further, for example, in a case where the time of a release operation is t2 that is different to t1, a pasting image Ip2 to which a, for example, blue frame is added is pasted and displayed at a corresponding position on the 3D model image M1, and with respect to the planar model image M2 also, the pasting image Ip2 is pasted and displayed at a corresponding position on the planar model image M2.

In such a case, on the planar model image M2, the pasting images Ip2 and Ip3 that were pasted at different timings are displayed in a manner in which the pasting images Ip2 and Ip3 can be distinguished from each other. Accordingly, the planar model image generating portion 31f constituting the expanded image generating means forms means for displaying in a distinguishable manner the image pickup images (endoscopic images) that are pasted on the planar model image M2 based on positional information of the image pickup portion 23.

Further, in the present embodiment, in a case where a set time period that is previously set elapses, displaying (presenting) of pasting images that were pasted on the 3D model image M1 is stopped, and all the pasting images are displayed (presented) on the planar model image M2 with respect thereto. Note that, a configuration may also be adopted that, together with a condition of being within a set time period, limits the number of pasting images to be pasted and displayed on the 3D model image M1.

By displaying the pasting images as shown in FIG. 11, similarly to the case of the first embodiment, the pasting images can be presented in a state that makes it easy for the surgeon to ascertain the relation with the insertion form and thus performance of examination or treatment of a lesion site or the like can be facilitated. Further, since a configuration is adopted so as to paste pasting images on the 3D model image in a manner that takes into consideration three-dimensional positional and directional information in a case where an image of the inner surface of the bladder B is picked up, the positional relation with a site such as a lesion site that the surgeon wants to attempt to examine can be easily ascertained, and smooth performance of examination or treatment inside the bladder can be facilitated.

In addition, in the present embodiment, ascertainment of all endoscopic images that were recorded by performing release operations can be easily ascertained by means of the pasting images that are pasted on the planar model image M2. For example, if a lesion site exists, based on the display of all the pasting images, the surgeon can easily ascertain whether or not the lesion site and sites around the lesion site have been recorded.

Further, since a configuration is adopted so as to limit the number of pasting images that are pasted and displayed on the 3D model image M1 within a set time period, the shape of the insertion form image Ii is not hidden due to the presence of too many pasting images, and a state in which the insertion form is easily ascertained can be ensured.

Note that, although in the foregoing description an example is described in which, in a case of pasting an endoscopic image obtained at the time of a release operation on the 3D model image M1 and the planar model image M2, a frame of the same color is added to and displayed (presented) with the same pasting images, the following configuration may also be adopted.

Instead of adding frames of the same color (making the color of the frames the same) as described above, a configuration may also be adopted so as to attach the same character or symbol. In this case, different characters or symbols are attached for each release operation so that images pasted at different timings can be distinguished.

Alternatively, a configuration may be adopted so that, in a case where a pasting image on one of the model images is specified using a keyboard or a mouse or the like, the relevant image is highlighted and, further, the corresponding pasting image on the other model image is also highlighted. As a specific display method for highlighting a pasting image, for example, the specified pasting image (and corresponding pasting image) are surrounded by a thick frame and displayed. Alternatively, a configuration may be adopted that decreases the chroma of other pasting images to thereby make it easy to distinguish the specified pasting image (and corresponding pasting image).

Third Embodiment

Figure 12:
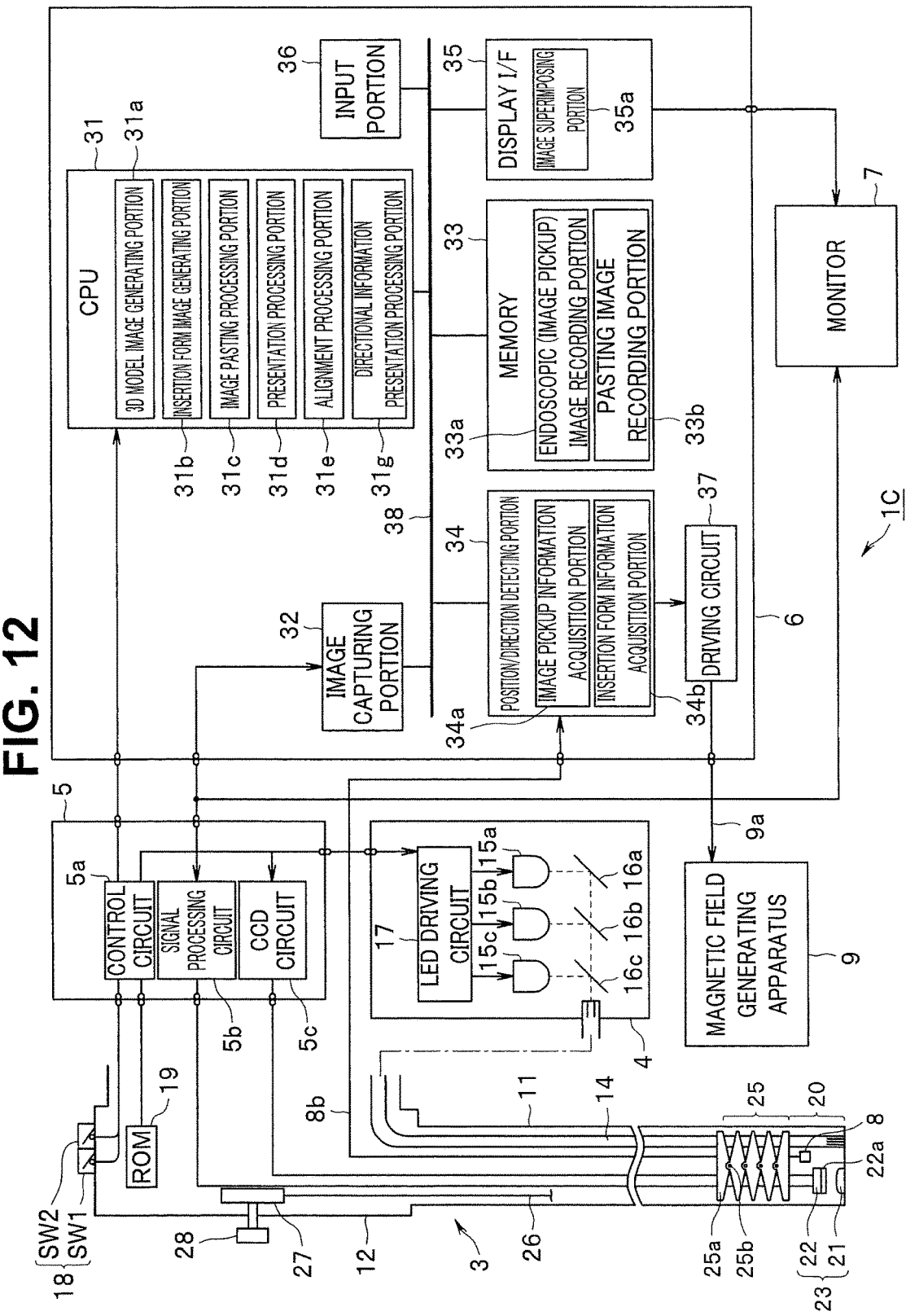
FIG. 12 is a view illustrating the internal configuration of an endoscope system according to a third embodiment of the present invention.

Next, a third embodiment of the present invention will be described. FIG. 12 illustrates an endoscope system 1C of the present embodiment. Relative to the endoscope system 1 of the first embodiment that is shown in FIG. 2, in the endoscope system 1C, for example, the CPU 31 further includes a function of a directional information presentation processing portion (or a directional information presentation processing circuit) 31g that performs processing to present, on the current endoscopic image, directional information representing a direction in which a specific site exists on the 3D model image. The signal processing circuit 5b or the presentation processing portion 31d that performs processing to present the endoscopic image (image pickup image) may be configured to include the function of the directional information presentation processing portion 31g. The remaining configuration is the same as the first embodiment.

Figure 13A:
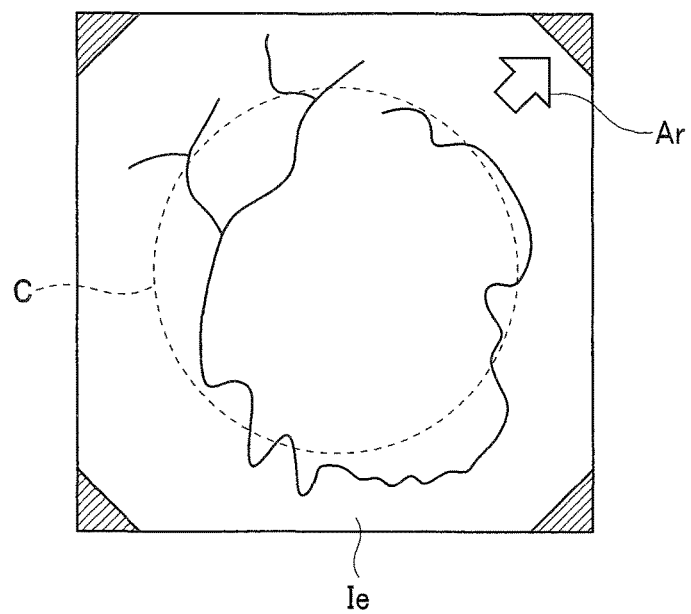
FIG. 13A is a view illustrating an endoscopic image in which an arrow is displayed as directional information indicating a direction in which a lesion site is present.

FIG. 13A illustrates a state in which, on the endoscopic image Ie, an arrow Ar is displayed as directional information that indicates a direction in which, for example, a lesion site as a specific site on which the surgeon is focusing attention is present on the 3D model image. Note that, in the case of displaying (presenting) directional information, since in most cases the directional information is displayed (presented) after an image of, for example, a lesion site as a specific site on which the surgeon is focusing attention is picked up, it can also be said that the directional information presentation processing portion 31g performs processing to present, on the current endoscopic image Ie, directional information that indicates a direction in which a specific endoscopic image (image pickup image) obtained by picking up an image of a specific site is present on the 3D model image.

The directional information presentation processing portion 31g performs processing to calculate a vector oriented in the direction of the arrow Ar as described hereunder, and displays the arrow Ar along the direction of the vector at a portion on a peripheral side (for example, excluding an area within a fixed range from the center of the screen) on the current endoscopic image Ie.

In the display example in FIG. 13A, it is shown that a lesion site or an image of a lesion site is present in the upper right direction that is indicated by the arrow Ar. Further, in FIG. 13A, a configuration is adopted so as not to display the arrow Ar as directional information within a fixed range (specifically, a circle C indicated by a dashed line) from the center of the screen. Note that, the circle C is used to indicate a range in which the arrow Ar is not displayed, and the circle C is not displayed on the actual endoscopic image Ie.

Figure 13B:
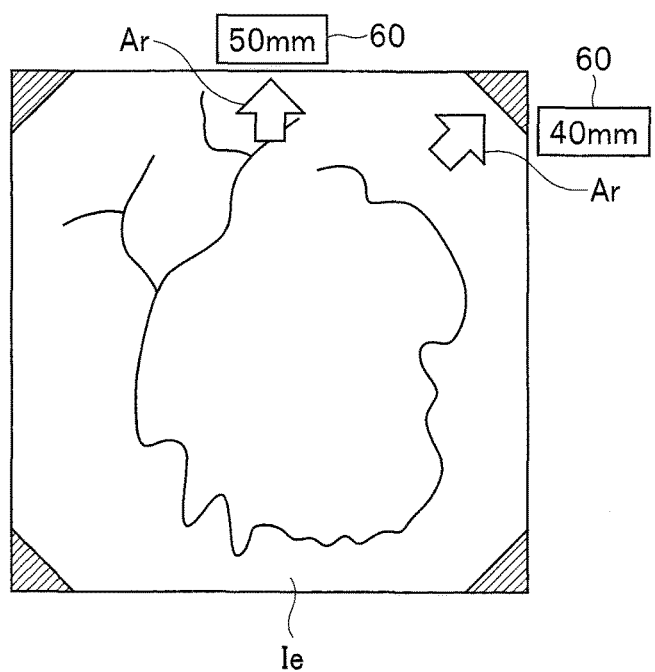
FIG. 13B is a view illustrating an endoscopic image in which, in addition to arrows as directional information, distance information showing a distance to another lesion site (or an image thereof) is displayed.

Note that, as shown in FIG. 13B, together with the arrow Ar information showing a distance to the lesion site may also be displayed. For example, with respect to the case in FIG. 13A, if the distance to the lesion site is 40 mm, as shown in FIG. 13B, distance information 60 to the effect that the distance is 40 mm is displayed together with the arrow Ar.

Further, in a case where a lesion site is present, for example, at a distance of 50 mm in the upward direction, as shown in FIG. 13B, distance information 60 to the effect that the distance is 50 mm is displayed together with the arrow Ar. By adopting such a configuration, together with the direction in which the lesion site exists, the surgeon can also ascertain the distance thereto, thereby facilitating smooth performance of examination or treatment of a lesion site or the like inside the bladder B.

Further, instead of specifically displaying the distance as shown in FIG. 13B, a configuration may be adopted so as to change the length, size or color of the arrow Ar according to the distance to the lesion site.

Figure 14:
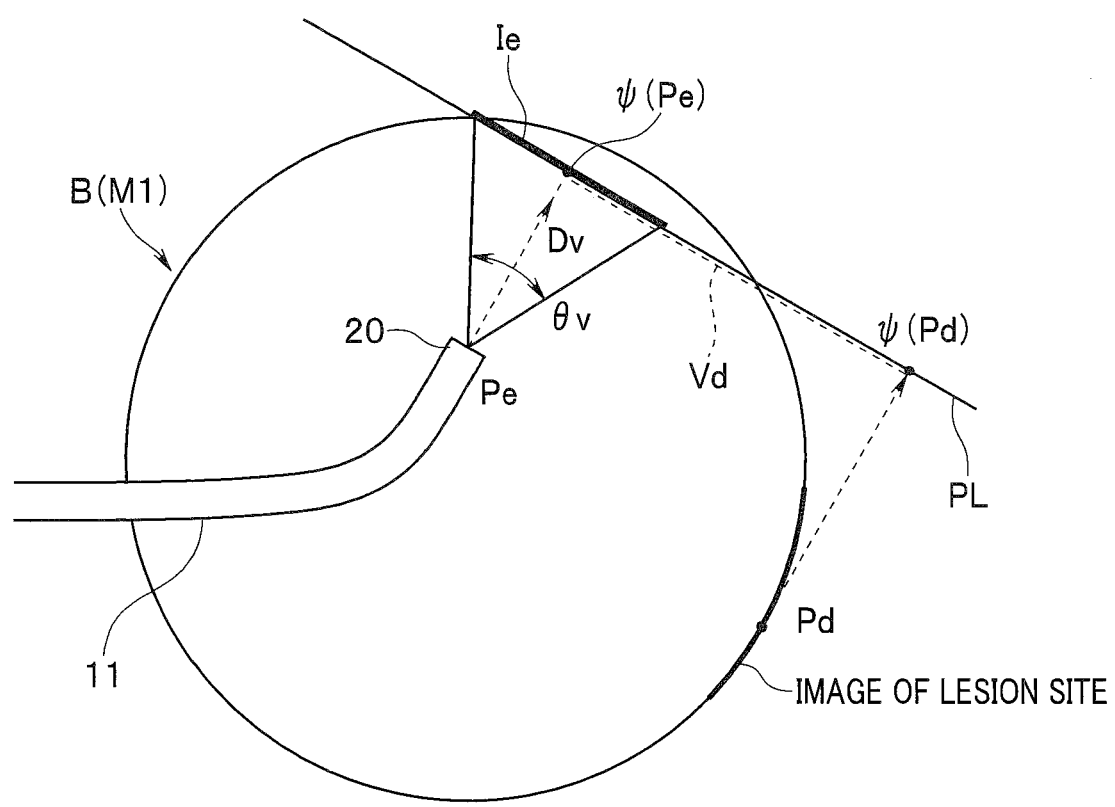
FIG. 14 is an explanatory view for calculating a direction in which a lesion site exists and a vector representing a distance.

FIG. 14 illustrates an explanatory drawing for calculating the direction of the aforementioned arrow Ar and a vector that represents the distance. In FIG. 14, a plane PL that includes an endoscopic image Ie corresponding to an optical image that is picked up by the image pickup portion 23 (not shown in FIG. 14) inside the distal end portion 20 and is formed on the image pickup surface of the image pickup portion 23 is schematically shown on 3D model image M1. The endoscopic image Ie is parallel to the image pickup surface of the image pickup portion 23, and is perpendicular to the line of sight direction Dv of the image pickup portion 23.

In correspondence with the size of the endoscopic image, the view angle θv and the line of sight direction Dv, the plane PL that includes the aforementioned endoscopic image Ie is expressed by $$ax+by+cz+d=0 \quad (1)$$

Where, n=(a, b, c) is a vector representing the line of sight direction Dv.

If a given point P(p) (=P (p1, p2, p3)) on a three-dimensional space is projected onto the aforementioned plane PL in parallel with the line of sight direction Dv, a position ψ(P) thereof is $$\psi(P)=p-(d+p\cdot n)n/|n|^2 \quad (2)$$

Note that p is a vector representing the position of the point P(p). A point Pe of the distal end portion 20 and a point Pd at the center of the lesion site (or image of the lesion site) are substituted into the equation (2), and the direction of a vector Vd connecting two points (positions) ψ(Pe) and ψ(Pd) that are projected onto the plane PL from ψ(Pe) to ψ(Pd) is the direction of the arrow Ar. Further, |ψ(Pd)−ψ(Pe)| corresponds to a distance from (the position ψ(Pe) that is close to the center of) the endoscopic image Ie to the position ψ(Pd) on the plane of projection of the point Pd at the center of the lesion site (or image of the lesion site), on the plane PL that includes the endoscopic image Ie. Note that, in the case of displaying the distance information as shown in FIG. 13B, the distance on the plane PL including the endoscopic image Ie may be displayed, the position ψ(Pe) may be regarded as a position on the 3D model image M1 and a distance along the spherical surface of the 3D model image M1 (distance from the position ψ(Pe) to the position Pd measured along the spherical surface) may be displayed, or |Pd−Pe| may be displayed.

The present embodiment has the same actions and advantageous effects as the first embodiment, and furthermore, because a direction in which a specific site such as a lesion site on the current endoscopic image is present on the 3D model image M1 is displayed (presented), the surgeon can easily know the direction in which a lesion site or the like exists. Further, in a case where distance information is displayed, it becomes even easier to approach a position at which a specific site such as a lesion site exists.

Furthermore, since the arrow Ar is displayed on the endoscopic image, while observing the endoscopic image, the surgeon can easily know the direction in which a lesion site or the like exists without the surgeon moving their line of sight.

Also, because the arrow Ar is displayed on the side of a peripheral site on the endoscopic image, the visibility of the endoscopic image need not be reduced (a reduction in visibility can be prevented).

Figure 13C:
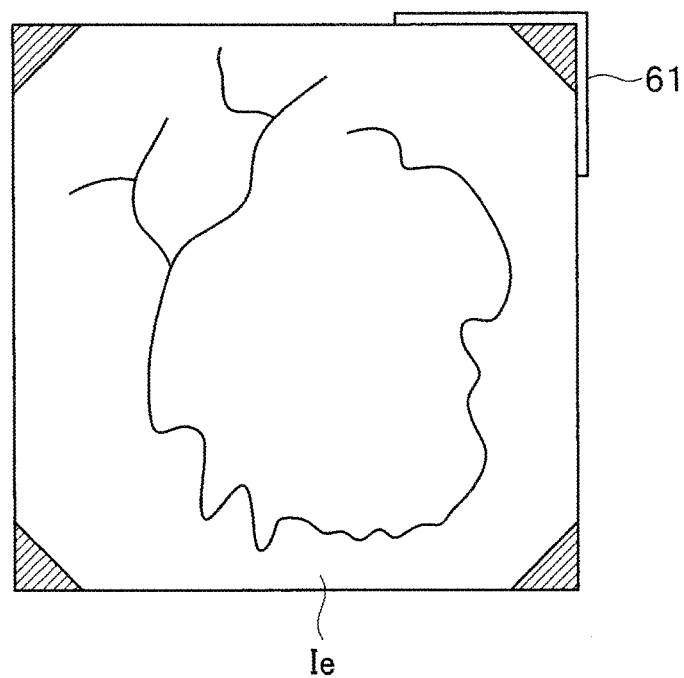
FIG. 13C is a view illustrating an endoscopic image in which directional information of a different form to the arrow shown in FIG. 13A is displayed.

Note that, although the arrow Ar is displayed in FIG. 13A and the like as directional information, for example, as shown in FIG. 13C, a configuration may be adopted in which the direction of a specific site such as a lesion site is shown by a color 61 or the like that is added to an edge of the endoscopic image Ie. Further, a configuration may also be adopted in which the approximate direction is indicated by the color 61 or the like added to an edge of the endoscopic image Ie.

In addition, a configuration may be adopted that changes the color 61 according to the distance to the specific site such as a lesion site.

Furthermore, as the directional information, instead of the arrow Ar or the like, for example, a symbol such as "○", "□" or "Δ" may be displayed at a position that corresponds to the distal end of the arrow. Further, for example, the symbol to be displayed may be changed in the manner ○→□→Δ as the distance to a specific site such as a lesion site increases.

The size or color of a symbol that is displayed may also be changed according to the distance to a specific site such as a lesion site.

Further, in the present embodiment, although an example has been described in which directional information is displayed (presented) on the current endoscopic image, a configuration may also be adopted so as to display (present) directional information when any one or more of the following conditions (a) to (e) are satisfied:

(a) when a trigger signal is inputted that is generated at a time a user such as the surgeon operated a keyboard, a touch panel, a scope switch, a foot switch, an operation panel or the like;

(b) when a user such as the surgeon specified a lesion (site);

(c) when a distance to a lesion (site) is within a previously set distance;

(d) when a distance from the distal end portion of the endoscope to the inner surface of the 3D model image M1 is within a previously set distance (a distance from the distal end portion of the endoscope to the inner surface of the 3D model image M1 is calculated, for example, utilizing the principles of stereo measurement); and (e) when a certain lesion (site) is present in the vicinity of the current endoscopic image.

In this way, a configuration may be adopted that displays directional information only in a case where a predetermined condition is satisfied.

If settings are made so as to display directional information only when a predetermined condition is satisfied in this manner, there is the advantage that a user such as the surgeon can select the display of directional information in accordance with the settings or preferences of the user or the like.

Note that, although a case has been described in which, as the endoscope system 1C of the third embodiment, the directional information presentation processing portion 31g that presents directional information is also provided with respect to the endoscope system 1 of the first embodiment, a configuration may also be adopted in which the directional information presentation processing portion 31g is also provided with respect to the endoscope system 1B of the second embodiment. In such a case, as well as having the same actions and advantageous effects as the second embodiment, because a direction in which a specific site such as a lesion site on the current endoscopic image exists on the 3D model image M1 is also displayed (presented), the surgeon can easily know the direction in which a lesion site or the like exists.

Fourth Embodiment

Figure 15:
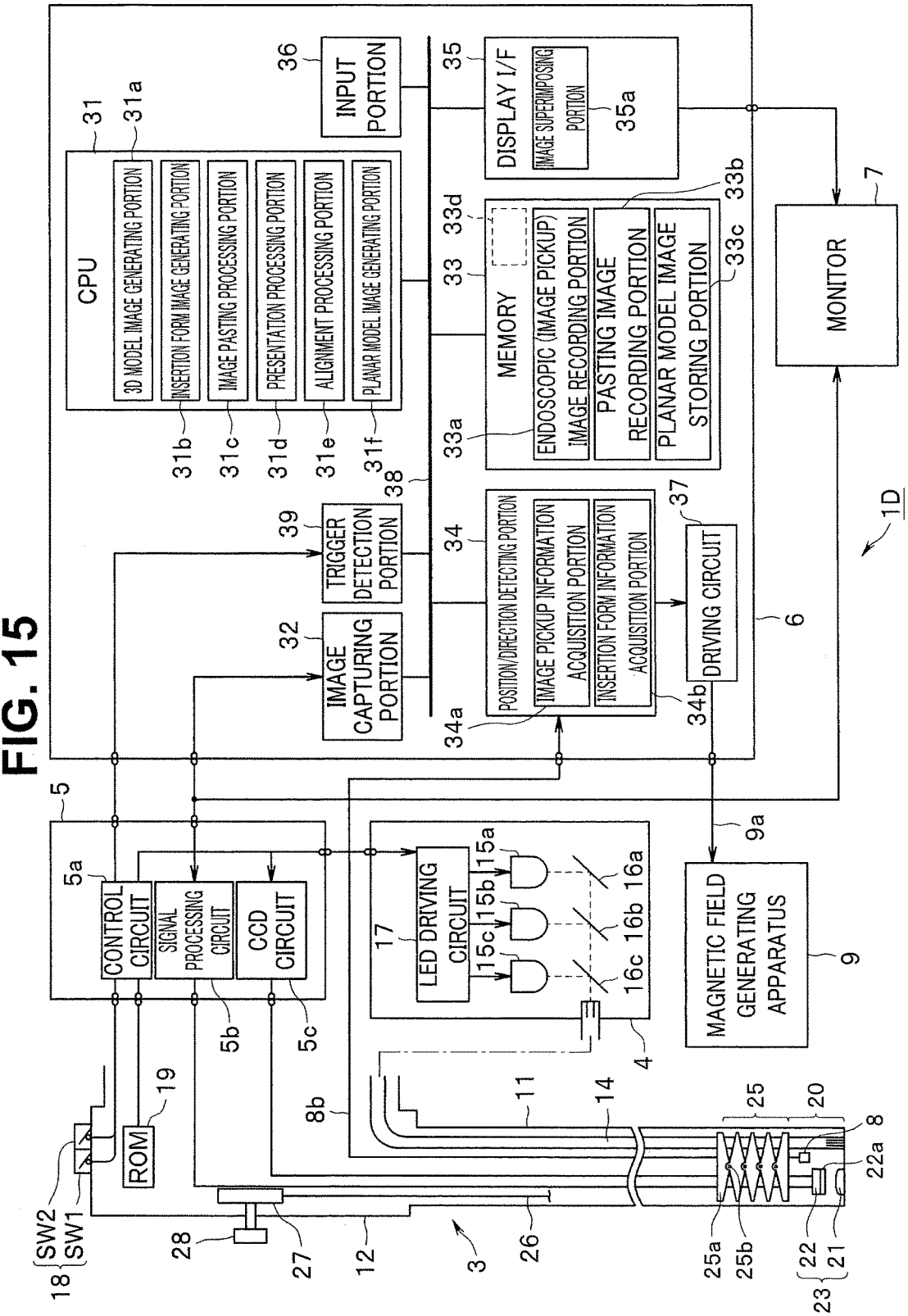
FIG. 15 is a view illustrating the internal configuration of an endoscope system according to a fourth embodiment of the present invention.

Next, a fourth embodiment of the present invention will be described. FIG. 15 illustrates an endoscope system 1D of the fourth embodiment. For example, relative to the endoscope system 1B of the second embodiment that is illustrated in FIG. 8, in the endoscope system 1D, a trigger detection portion (or trigger detection circuit) 39 that detects switching of the observation mode or the like as a trigger signal is also provided in the image processing apparatus 6.

The trigger detection portion 39 is connected to the control circuit 5a of the processor 5, and detects an instruction to switch the observation mode that is inputted from the mode switching switch SW1, and detects an instruction of a user such as the surgeon, such as an instruction to switch the planar model image M2. The trigger detection portion 39 sends the detected trigger signal to the CPU 31, and the CPU 31 performs corresponding control processing.

Note that, since a user such as a surgeon can also input an instruction to switch the planar model image M2 from the input portion 36 that is provided in the image processing apparatus 6, a configuration may also be adopted in which the trigger detection portion 39 also detects a signal that is inputted from the input portion 36.

Furthermore, in the present embodiment, to enable use of a planar model image that corresponds to the observation mode that is actually being used, for example, the memory 33 has a function of a planar model image storing portion 33c that stores a plurality of planar model images that correspond to a plurality of observation modes. Note that, the planar model image storing portion 33c may also be provided in a storage device or the like that is a separate device to the memory 33.

Specifically, the planar model image storing portion 33c stores a planar model image for the WLI mode, and a planar model image for the NBI mode as a concrete example of the special light observation mode. When release operations are performed in the respective observation modes, pasting images are pasted on the planar model images for the respective observation modes. Accordingly, since release operations are performed at different times in the two observation modes, the planar model images are different to each other. Further, when a release operation is performed in each observation mode and a pasting image is pasted on the relevant planar model image and the planar model image changes, the planar model image is stored in the planar model image storing portion 33c. That is, the planar model image that is stored in the planar model image storing portion 33c is updated over time.

Figure 16A:
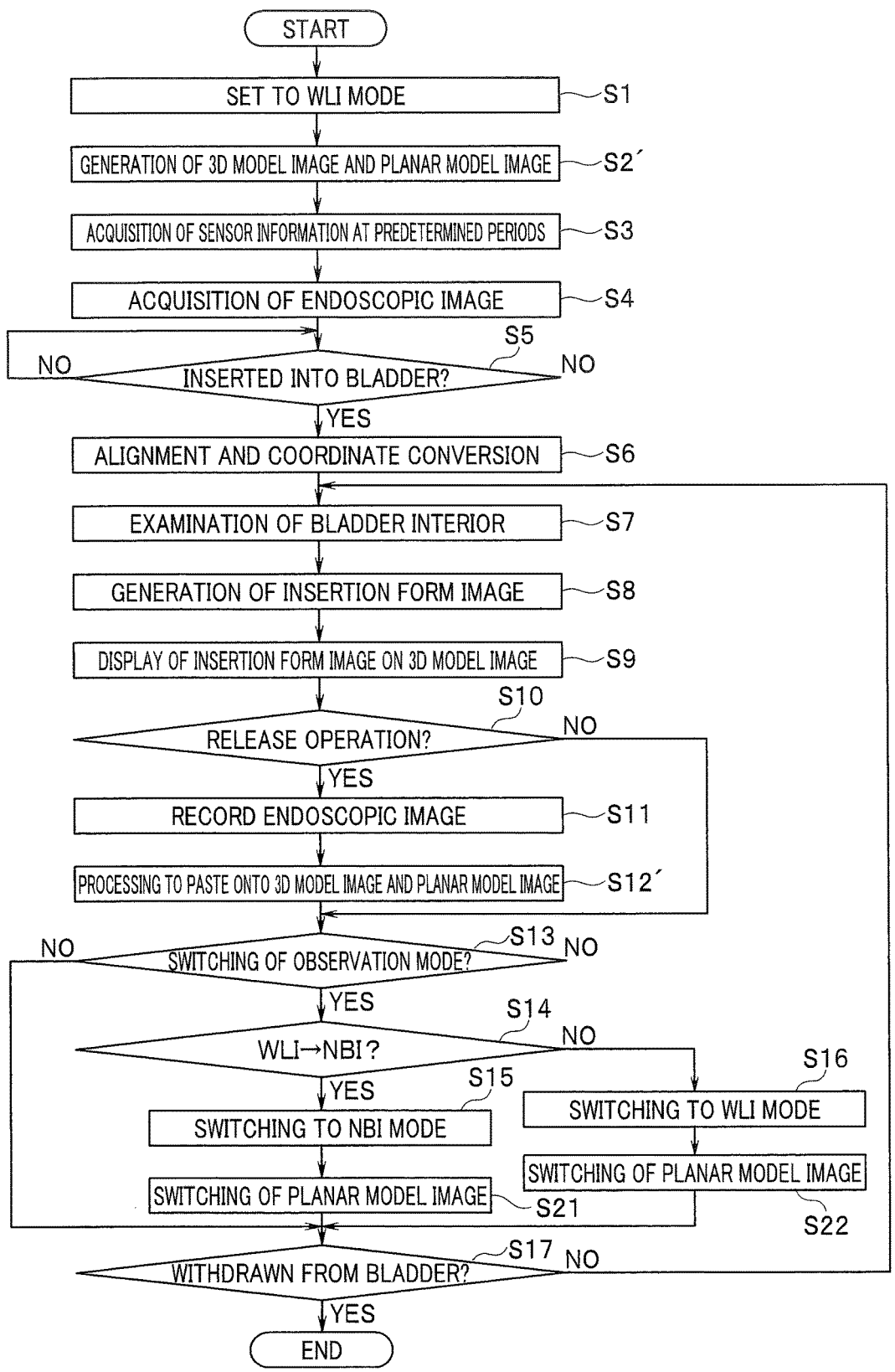
FIG. 16A is a flowchart illustrating a processing example of the fourth embodiment.

Typical operations in the present embodiment are illustrated in a flowchart in FIG. 16A. Relative to the flowchart in FIG. 10, in the flowchart in FIG. 16A, the processing in step S21 that is provided between step S15 and step S17, and the processing in step S22 that is provided between step S16 and step S17 are performed. In step S21, the trigger detection portion 39 detects switching of the observation mode to the NBI mode as a trigger signal, and sends the trigger signal for switching the observation mode to the CPU 31. Upon receiving the trigger signal, the CPU 31 switches the planar model image so as to use the planar model image that corresponds to the NBI mode. Note that, although switching of the planar model image is performed in correspondence to switching of the observation mode, because switching of the observation mode is accompanied by switching of the illuminating light, it can also be said that switching of a planar model image is performed in response to switching of the illuminating light (between normal light and special light such as narrow band light).

Further, in step S22, the trigger detection portion 39 detects switching of the observation mode to the WLI mode as a trigger signal, and sends the trigger signal for switching the observation mode to the CPU 31. Upon receiving the trigger signal, the CPU 31 switches the planar model image so as to use the planar model image that corresponds to the WLI mode.

After switching of the planar model image in steps S21 and S22, in a case where withdrawal of the distal end portion 20 from the bladder is not performed in step S17, the operation returns to the processing in step S7, and for example, as shown in step S10, the existence/non-existence of a release operation is determined, and if a release operation is performed an endoscopic image is pasted on the planar model image that was switched to, and is also pasted on a 3D model image. Further, the planar model image is stored in the planar model image storing portion 33c.

According to the present embodiment, as well as having the same actions and advantageous effects as in the second embodiment, because a configuration is adopted so as to also switch the planar model image according to the observation mode, in a case where the bladder B as the predetermined organ is being examined or the like using a plurality of observation modes also, the state recorded in the respective observation modes can be easily ascertained.

In the processing shown in FIG. 16A, although a configuration is adopted so that, when switching of the observation mode is performed, a planar model image is adopted that corresponds to the observation mode that is selected by the switching, a configuration may also be adopted so that, when switching of the observation mode is performed, the planar model image and the 3D model image are switched in conjunction with one another. Further, in this case, together with the planar model image storing portion 33c that stores a plurality of planar model images that correspond to a plurality of observation modes, it is good to also provide a 3D model image storing portion 33d that stores a plurality of stereoscopic model images (3D model images) that correspond to a plurality of observation modes. Note that, in FIG. 15, the 3D model image storing portion 33d is indicated with a dashed line.

As the characteristic configuration contents in this case, the endoscope system includes: observation mode switching means for performing switching between two observation modes that are a first observation mode in which an image pickup operation by image pickup means is performed under illumination of normal light with respect to a subject, and a second observation mode in which an image pickup operation by image pickup means is performed under illumination of a special light such as NBI; the 3D model image storing portion 33d that stores information of a first 3D model image and a second 3D model image as 3D model images that correspond to the two observation modes; and the planar model image storing portion 33c that stores information of a first planar model image and a second planar model image as the planar model images that correspond to the two observation modes. Further, in a case where a 3D model image and a planar model image are switched in conjunction with one another in response to switching of the observation mode and a release operation is performed, the image pasting processing portion 31c constituting image pasting means and the planar model image generating portion 31f constituting the expanded image generating means paste and present, for example, respective endoscopic images as image pickup images at a time that the release operation is performed, on a 3D model image and on an planar model image corresponding to the observation mode that is selected and switched to.

Further, a processing example in which a planar model image and a 3D model image are switched in conjunction with one another by switching of the observation mode according to the present modification is illustrated in FIG. 16B. In this case, the only differences relative to the processing flowchart in FIG. 16A are that steps S21 and S22 in FIG. 16A are replaced by steps S21' and S22', respectively. In steps S21' and S22', switching to a 3D model image and a planar model image for the NBI mode and switching to a 3D model image and a planar model image for the WLI mode are performed, respectively. That is, a configuration may be adopted so as to switch the planar model image and the 3D model image (in conjunction with one another) in response to switching of the observation mode or switching of the illuminating light. Further, when a release operation is performed after switching, as shown in step S12', an endoscopic image is pasted on the 3D model image and the planar model image in the observation mode that was switched to, and the 3D model image and planar model image on which the endoscopic image is pasted are updated and stored in the 3D model image storing portion 33d and the planar model image storing portion 33c, respectively.

In this case, since 3D model images corresponding to each of the observation modes are respectively adopted, pasting images in each observation mode can be checked on a 3D model image. The other advantageous effects are substantially the same as in the fourth embodiment. Note that, the contents that are mainly described in FIG. 16B may also be applied to, for example, the first embodiment.

Specifically, although in the first embodiment a 3D model image is used in a common manner when the observation mode is switched, as described in FIG. 16B a configuration may also be adopted so that, in response to switching of the observation mode, a 3D model image for the WLI mode or a 3D model image for the NBI mode is used in accordance with the mode that is selected by switching. That is, in the first embodiment, a configuration may be adopted in which the 3D model image may be switched in accordance with switching of the observation mode or switching of the illuminating light.

Although in the description of FIG. 16A it is described that only one planar model image that corresponds to the observation mode that is actually selected and used is displayed (presented), a configuration may also be adopted so as to display (present) the planar model image of all the observation modes. For example, in a case where the endoscope system includes an observation mode that has illumination means for switching between normal light and special light such as narrow band light and irradiating the light that is switched to, a configuration may be adopted in which, based on a trigger signal at a time that an image is picked up by image pickup means (or a trigger signal generated by an instruction operation performed by the user), the planar model image generating portion 31*f* or the presentation processing portion 31*d* as the expanded image generating means simultaneously presents two planar model images on which a normal light image that is picked up under illumination by normal light and a special light image that is picked up under illumination by special light are pasted, respectively.

In this case also, in a case where a release operation is performed and an endoscopic image is pasted, the endoscopic image is pasted on the planar model image of the observation mode that is actually selected and being used.

Further, a configuration may also be adopted in which a planar model image that is selected by the user such as a surgeon is displayed with priority over the other planar model image.

Figure 17:
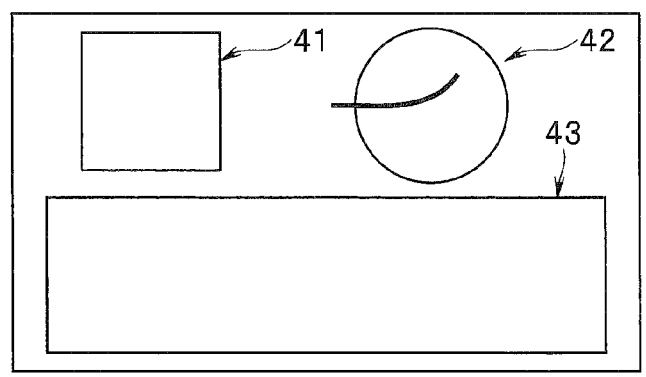
FIG. 17 is a view illustrating a display example of a planar model image according to a second modification of the fourth embodiment.
Figure 17:
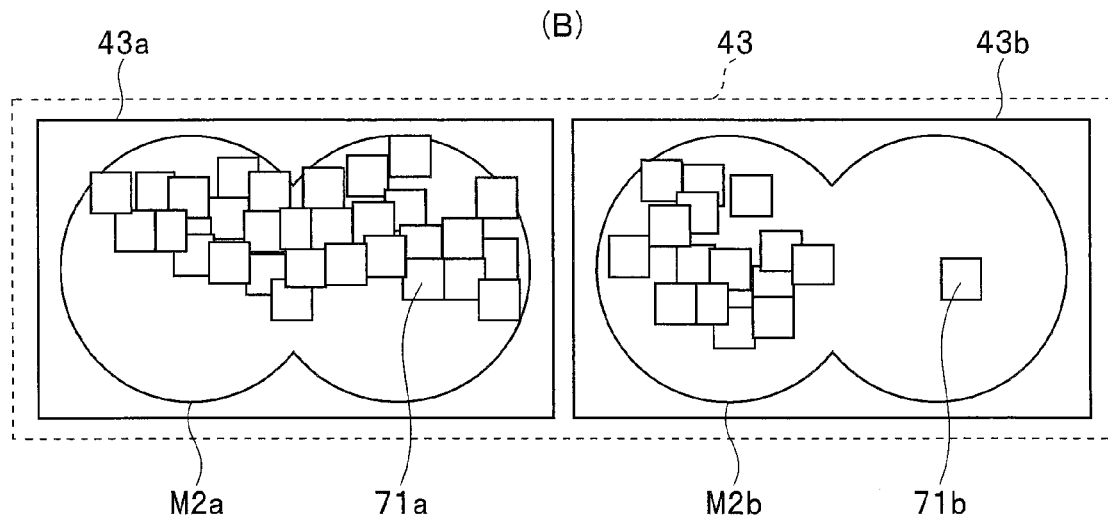

In the present embodiment a configuration may also be adopted as described in the following second modification. A plurality of planar model images are displayed at the same time, and a frame is displayed so that the current observation range (image pickup range) obtained by the image pickup portion of the endoscope can be distinguished even on a planar model image of an observation mode that is not currently selected. FIG. 17 shows display examples of the monitor 7 in this case. FIG. 17(A) shows an example of the arrangement of the first area 41, the second area 42 and the third area 43 on the display screen of the monitor 7.

In the present modification, for example, the third area 43 that includes two areas 43*a* and 43*b* is arranged on the lower section side of the display screen.

FIG. 17(B) illustrates display example portions in the two areas 43*a* and 43*b*. In the area 43*a* on the left side in FIG. 17(B), a planar model image M2*a* of the observation mode that is currently selected is displayed in a state in which pasting images are pasted thereon, while in the area 43*b* on the right side, a planar model image M2*b* of the observation mode that is not currently selected is displayed in a state in which pasting images are pasted thereon.

Further, in a case where an endoscopic image that is currently picked up by the image pickup portion 23 of the distal end portion 20 of the endoscope is pasted at a position indicated by reference character 71*a* as the result of a release operation, in the planar model image M2*b* of the observation mode that is not currently selected, a frame 71*b* is displayed that shows the current observation range (image pickup range). In a case where a release operation is performed, the position of the current observation range (image pickup range) can be confirmed even on the planar model image M2*b* of the observation mode that is not currently selected.

Note that, in a case where pasting of an endoscopic image is performed only in a case where a release operation is performed, a configuration may be adopted so as to display the frame 71*b* only in a case where a release operation is performed.

Figure 18:
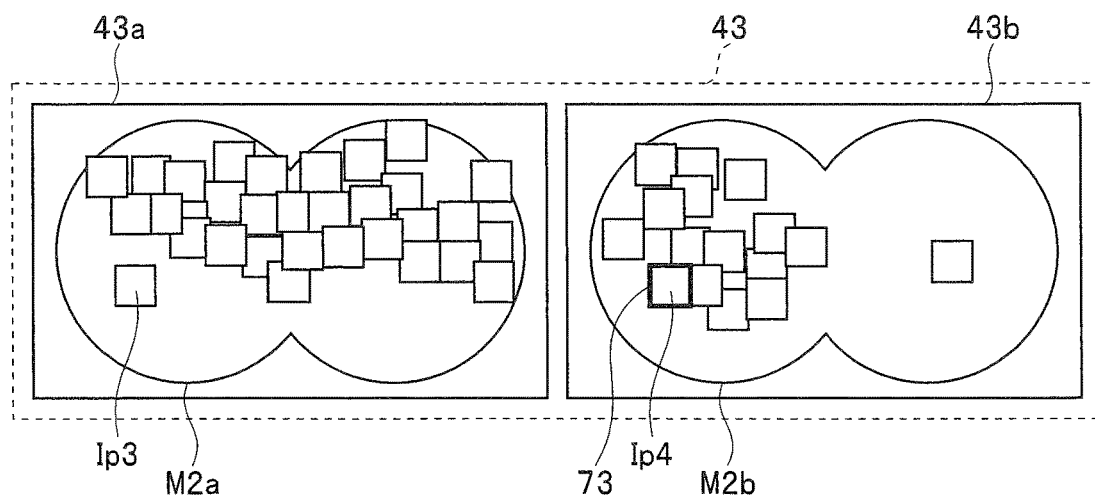
FIG. 18 is a view illustrating a display example of a planar model image according to a third modification of the fourth embodiment.

As a third modification with respect to the present embodiment, a configuration may be adopted so that, with respect to the observation mode that is not currently selected, in the case of a state in which the current observation range of the endoscope has already been observed and pasted as a pasting image, the already observed (already pasted) pasting image is highlighted. FIG. 18 illustrates a display example thereof.

In FIG. 18, for example, on the planar model image M2*a* of the observation mode that is currently selected that is displayed in the area 43*a* on the left side, when a release operation is performed an endoscopic image of the observation range that is currently being observed is pasted as a pasting image Ip3 at the position indicated in the drawing.

In this case, if the state is one in which the relevant observation range has already been observed in the observation mode that is not currently selected and is pasted as a pasting image Ip4 on the planar model image M2*b*, the edge of the pasting image Ip4 is colored with a color (indicated by a thick frame) 73 and displayed.

Note that, although a description regarding a case where a release operation has been performed is described with respect to FIG. 18, a configuration may also be adopted so as to similarly display the observation range that is currently being observed. Specifically, in a case where the observation range that is currently being observed is, for example, the position of the pasting image Ip3 on the planar model image M2*a*, the edge of the corresponding pasting image Ip4 on the planar model image M2*b* may also be colored with the color 73 and displayed.

Figure 19:
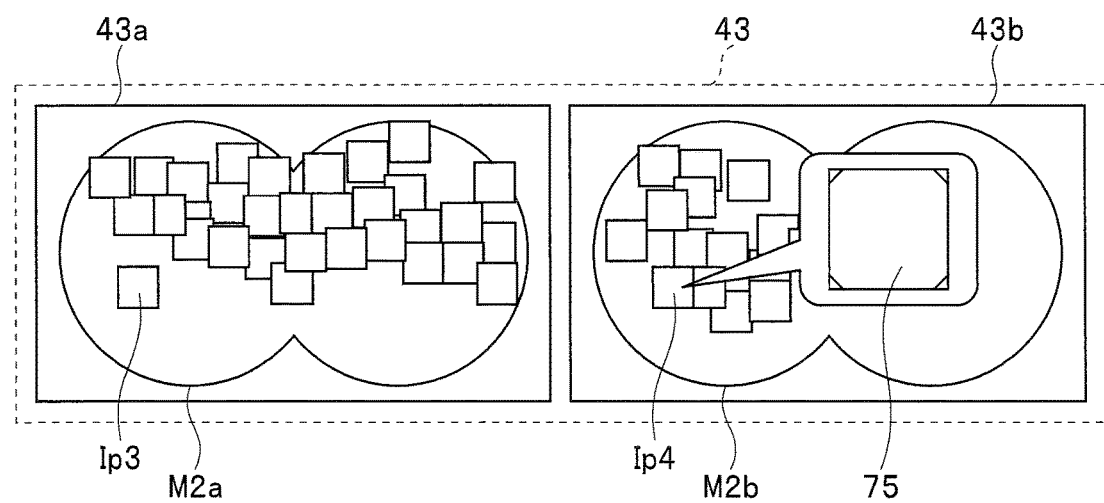
FIG. 19 is a view illustrating a display example of a planar model image according to the third modification of the fourth embodiment.

Instead of coloring with the color 73 and displaying, the corresponding pasting image Ip4 on the planar model image M2*b* may be, for example, displayed in an enlarged manner. FIG. 19 illustrates a display example in this case. The pasting image Ip4 at the position indicated in FIG. 18 is displayed as an enlarged image 75 in a display area that is indicated by a balloon.

Further, in a case where the pasting image Ip4 corresponding to the observation range that is currently being observed does not exist, a configuration may be adopted so as to display pasting images that exist in the vicinity thereof or an image that was already observed, such as a recorded endoscopic image.

Note that, although in the foregoing description it is described that the insertion form information acquisition means is provided in the vicinity of the image pickup means or in a member that is connected so as to maintain a predetermined positional relationship with the image pickup means, and acquires positional information regarding the image pickup means and insertion form information regarding the insertion form of the insertion portion that is inserted, a configuration may also be adopted in which the insertion form information acquisition means is provided in the vicinity of the image pickup means or in a member that is connected so as to maintain a predetermined positional relationship with the image pickup means, and acquires positional information regarding the distal end portion of the insertion portion and insertion form information regarding the insertion form of the insertion portion that is inserted.

Note that embodiments configured by, for example, partially combining the embodiments including the modifications that are described above also belong to the present invention.

What is claimed is:

1. An endoscope system, comprising:
    an endoscope comprising:
        an insertion portion configured to be inserted into a subject; and
        an image sensor configured to pick up an image of inside of the subject; and
    a processor comprising hardware, wherein the processor is configured to:
        acquire positional information of the image sensor;
        acquire insertion form information of the insertion portion inside the subject;
        on a three-dimensional model image that simulates a predetermined organ inside the subject, superimpose an insertion form image that is based on the insertion form information of the insertion portion inside the subject, and based on the positional information of the image sensor, also paste an image pickup image that is picked up by the image sensor, and present the three-dimensional model image; and present the image pickup image that is picked up by the image sensor and further, based on the positional information of the image sensor and specific image information among images that are pasted by the processor, present directional information indicating a direction in which the specific image information exists relative to the image pickup image.

2. The endoscope system according to claim 1, wherein the processor is configured to, on a planar model image in which a three-dimensional model image corresponding to the predetermined organ is planarly expanded, paste the image pickup image based on the positional information of the image sensor, and present the planar model image.

3. The endoscope system according to claim 2, wherein the processor is configured to control a display to display in a distinguishable manner the image pickup image that is pasted based on the positional information of the image sensor.

4. The endoscope system according to claim 2, further comprising:
a light source configured to switch between normal light and special light, and irradiate light that is switched to at the subject,
wherein the processor is configured to switch and present the planar model image in accordance with switching of the light source.

5. The endoscope system according to claim 2, further comprising:
a light source configured to switch between normal light and special light, and irradiate light that is switched to at the subject,
wherein, based on a trigger signal that is generated by an instruction operation of a user, the processor is configured to simultaneously present two planar model images onto which a normal light image that is picked up under illumination of normal light and a special light image that is picked up under illumination of special light are pasted, respectively.

6. The endoscope system according to claim 2, further comprising:
an observation mode switch configured to perform switching between two observation modes comprising a first observation mode in which an image pickup operation with respect to the subject is performed by the image sensor under illumination of normal light, and a second observation mode in which an image pickup operation with respect to the subject is performed by the image sensor under illumination of a special light;
a three-dimensional model image storage configured to store information of a first three-dimensional model image and a second three-dimensional model image as the three-dimensional model image that corresponds to the two observation modes; and
a planar model image storage configured to store information of a first planar model image and a second planar model image as the planar model image that corresponds to the two observation modes,
wherein in a case where the three-dimensional model image and the planar model image are switched in conjunction with one another in response to switching of the observation mode and a release operation is performed, the processor is configured to paste and present an image pickup image that is picked up at a time of the release operation on each of the three-dimensional model image and the planar model image that corresponds to an observation mode that is switched to.

7. The endoscope system according to claim 1, wherein the processor is configured to present the directional information in a case where the specific image is selected based on a trigger signal that is generated when a predetermined instruction operation by a user is detected.

8. The endoscope system according to claim 7, wherein together with the directional information indicating a direction in which the specific image information exists relative to the image pickup image, the processor is configured to present information showing a distance from the image pickup image to a position at which the specific image information exists.

9. The endoscope system according to claim 1, wherein the processor is configured to present a current image pickup range in which an image is being picked up inside the predetermined organ by the image sensor at a corresponding position on the three-dimensional model image.

10. The endoscope system according to claim 1, further comprising:
wherein the processor is configured to, in a case where the insertion portion is inserted inside the predetermined organ, convert the positional information of the image sensor from a first coordinate system that is used in a case where the processor acquires the positional information to a second coordinate system that is set by adopting a reference position of the predetermined organ as an origin.

11. The endoscope system according to claim 1, wherein the processor is configured to change a size of the image pickup image that is picked up by the image sensor in accordance with a distance between the subject and a distal end portion of the insertion portion, and paste the image pickup image on the three-dimensional model image.

12. An endoscope system comprising:
an endoscope comprising:
an insertion portion configured to be inserted into a subject; and
an image sensor configured to pick up an image of inside of the subject; and
a processor comprising hardware, wherein the processor is configured to:
acquire positional information of the image sensor;
acquire insertion form information of the insertion portion inside the subject;
on a three-dimensional model image that simulates a predetermined organ inside the subject, superimpose an insertion form image that is based on the insertion form information of the insertion portion inside the subject, and based on the positional information of the image sensor, also paste an image pickup image that is picked up by the image sensor, and present the three-dimensional model image; and
paste the image pickup image that is picked up by the image sensor in a state in which a distal end portion of the insertion portion is inserted into the predetermined organ onto an image of spherical three-dimensional model simulating the predetermined organ that is drawn with a wire frame, in a size that approximately matches a range in which the image pickup image is picked up, at a position at which the image is picked up by the image sensor, wherein:
in a case of pasting the image pickup image that is obtained by picking up an image of an inner surface of the predetermined organ by means of the image sensor as a pasting image on a substantially spherical surface of the three-dimensional model image, the three-dimensional model image has a first pasting face on which the pasting image is pasted in a manner that enables a user to observe an image surface side of the pasting image, and a second pasting face on which the pasting image is pasted in a manner that enables the user to observe a rear surface side of the image surface of the pasting image, and the processor is configured to paste and present as the pasting image an image that is obtained by inverting left/right directions of the image pickup image on the second pasting face.

* * * * *